(12) United States Patent
Fukui

(10) Patent No.: US 7,305,265 B2
(45) Date of Patent: Dec. 4, 2007

(54) HEART TREATMENT EQUIPMENT FOR TREATING HEART FAILURE

(75) Inventor: Yoshihito Fukui, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 571 days.

(21) Appl. No.: 10/718,533

(22) Filed: Nov. 24, 2003

(65) Prior Publication Data

US 2004/0172074 A1    Sep. 2, 2004

(30) Foreign Application Priority Data

Nov. 25, 2002   (JP)   ............................. 2002-341368
Dec. 5, 2002    (JP)   ............................. 2002-353838

(51) Int. Cl.
    *A61N 1/368* (2006.01)
(52) U.S. Cl. ............................................ 607/9; 607/15
(58) Field of Classification Search .................... 607/4, 607/9, 14, 15, 36
    See application file for complete search history.

(56) References Cited

U.S. PATENT DOCUMENTS

| | | | |
|---|---|---|---|
| 4,928,688 A | 5/1990 | Mower | |
| 5,199,428 A | 4/1993 | Obel et al. | |
| 5,203,326 A | 4/1993 | Collins | |
| 5,330,507 A | 7/1994 | Schwartz | |
| 5,578,061 A | 11/1996 | Stroetmann et al. | |
| 5,658,318 A | 8/1997 | Stroetmann et al. | |
| 5,700,282 A | 12/1997 | Zabara | |
| 6,233,079 B1 | 5/2001 | Miyamori | |
| 6,522,923 B1* | 2/2003 | Turcott | 607/27 |
| 6,842,642 B2* | 1/2005 | Vanhout | 607/15 |
| 2001/0049543 A1* | 12/2001 | Kroll | 607/28 |
| 2003/0078623 A1* | 4/2003 | Weinberg et al. | 607/9 |

* cited by examiner

*Primary Examiner*—Kennedy J. Schaetzle
*Assistant Examiner*—Natasha Patel
(74) *Attorney, Agent, or Firm*—Buchanan Ingersoll & Rooney PC

(57) ABSTRACT

In a heart treatment equipment provided with a stimulating mechanism for both the ventricles, the both ventricle stimulation is made optimized in order to inhibit the decrease of the cardiac output when a heart rate increase or the vagus nerve stimulation is performed and the equipment comprises a right ventricle pulse generator for stimulation the right ventricle, a left ventricle pulse generator for stimulation the left ventricle, wherein the controller for selecting either one of aforesaid right ventricle pulse generator and left ventricle pulse generator or selecting both of them for the ventricle stimulation is constituted such as to select both of the right ventricle pulse generator and the left ventricle pulse generator in response to the vagus nerve stimulation or the heart rate monitor output.

9 Claims, 11 Drawing Sheets

HEART TREATMENT EQUIPMENT FOR TREATING HEART FAILURE

BACKGROUND OF THE INVENTION

1. Field of the Invention

The present invention relates to a heart treatment equipment for treating a heart failure and more particularly to a heart treatment equipment where a heart failure is treated in such a way that right and left ventricles are stimulated at the same time in response to the stimulation of the vagus nerve or the heart rate increase.

2. Description of the Related Art

A cardiac activity is put under the antagonistic control of an automatic nervous system and the automatic nervous system has a sympathetic nerve and a parasympathetic nerve where the parasympathetic nerve of the heart is a vagus nerve and the increase in the sympathetic tone has an excitatory effect on the cardiac activity and the increase in the vagal tone has an inhibitory effect on the cardiac activity.

The inhibitory effect on cardiac activity by the increase of the vagal tone mainly causes a decrease of the heart rate and the arterial blood pressure. The decrease of the heart rate reduces the number of a ventricular premature contraction and the like which induce a ventricular tachycardia and a ventricular fibrillation. The decrease of the arterial blood pressure reduces myocardial oxygen consumption correlatively with the decrease of the heart rate. The decrease myocardial oxygen consumption prevents a myocardial infarction and at the same time prevents the myocardial failure region and its peripheral region from becoming oxygen-deprived. The increase of the vagal tone also suppresses the sympathetic tone directly.

By utilizing such a principle, it is shown a heart treatment equipment in Japanese laid-open patent publication No. 8-38625 (corresponding to U.S. Pat. No. 5,578,061) where the vagus nerve is stimulated and at the same time the sympathetic nerve is stimulated for the purpose of a sympathetic nerve block in response to the detection of the tachyarrhythmia so as to prevent and to treat a tachyarrhythmia.

Further, a heart treatment equipment for stabilizing the cardiac rhythm (heart rate) and for maintaining the cardiac rhythm (heart rate) in the free running cycle of the heart by electrically stimulating the vagus nerve and the sympathetic nerve at the same time was also already proposed (see, for example, a Japanese laid-open PCT patent publication No. 11-514268, which corresponds to U.S. Pat. No. 5,700,282).

The electric stimulation of the vagus nerve has such as an effect of decreasing the cardiac conduction velocity and an effect of decreasing ventricle contraction force caused by a negative inotropic effect other than decreasing the heart rate and the arterial blood pressure. The electric stimulation of the vagus nerve also made distribution of the cardiac conduction velocity non-uniform in the ventricle in connection with the region and the seriousness about the myocardial injury and/or disease of the organic heart disease, so that there was a problem of causing a cardiac conduction disturbance. For example, when a phenomenon where a cardiac conduction system cannot conduct a impulse to the right ventricle or the left ventricle or a phenomenon where a conduction of a impulse is delayed occurs, the efficient blood ejection based on a harmonic contraction of the right ventricle and left ventricle cannot be achieved, so that the heart pumping dysfunction develops. As a result, the cardiac output decreases and an organic heart disease patient whose cardiac function is lowered decreased would have a further deterioration of cardiac function and develops a heart failure. Similarly, the decreasing of a ventricle contraction force caused by a negative inotropic effect would develop a heart failure.

A heart failure means a condition that the heart loses its ability to pump enough blood which is suitable for a metabolism demand and it is caused by various heart diseases and mainly by an ischemic heart disease, a cardiac myopathy, heart valve disease and the like. For many of heart failure patients, a paradoxical movement of a ventricular septum occurs caused by an intra-ventricular conduction disturbance of such as a bundle branch block and an abnormal delay, so that the cooperative contraction of the right and left ventricles is inhibited and the cardiac output is decreased.

In the U.S. Pat. No. 4,928,688 specification, there is shown a heart failure treatment equipment where the right ventricle and the left ventricle are stimulated simultaneously or stimulated with shifted timings in order to recover the cooperative contraction of the right and left ventricles. According to the equipment shown in this patent document, there is shown an equipment where the right and left ventricles are stimulated simultaneously based on heart signals detected from the right ventricle and left ventricle respectively if a ventricular contraction is not detected from either of the right and left ventricles and when the contraction is detected in either one of the ventricles, the heart signal of the ventricular from which the ventricular contraction is not detected will be observed for a short period after that detected time point and that ventricular is stimulated if the ventricular contraction will not be detected.

Further, a method is known where each of mechanical contractions of the right ventricle and the left ventricle and the left ventricle cardiac output are detected by an impedance measurement and the timing of the relative left ventricle stimulation is adjusted for the mechanical contraction of the right ventricle such that the left ventricle cardiac output will become a maximum value (see, for example, the U.S. Pat. No. 6,223,079 specification).

A paradoxical movement of a ventricular septum prevents an effective blood ejection of the ventricle and decreases the stroke volume, so that the heart intends to compensate a necessary cardiac output by an increase of a heart rate such that the heart rate will be maintained high as compared with a normal condition. In case when the pump function of the ventricle cannot follow this increase of a heart rate, the increase of the cardiac output cannot be expected and what is even worse, the cardiac output may decrease oppositely. Therefore, there was a problem that the rapid increase in a heart rate occurs for a heart failure patient even in minimal exertion and he cannot continue exertion such that he feels palpitation, fatigue and the like owing to a fact that the pump function of the ventricle cannot follow this increase of a heart rate.

Further, the stimulation voltage of the left ventricle is generally set at a voltage level over several times as compared with that of the stimulation voltage of the right ventricle. This is because the left ventricle is usually stimulated through a vessel wall of the coronary vein by inserting an electrode lead intravenously to the coronary sinus such that the stimulation threshold itself becomes very high while the right ventricle is stimulated by an electrode which directly contacts the cardiac muscle. Additionally, it is difficult for the left ventricle stimulation to fix the electrode at an aimed region of the coronary sinus and there is a possibility of transferring the electrode after fixed, so that a large margin is set for the stimulation voltage relative to the stimulation threshold in order to surely carry out the stimulation. As a result, the electric power consumption of the left ventricle stimulation increases very much, so that the electric power consumption for the stimulation of both the ventricles where the right ventricle and the left ventricle are stimulated at the same time becomes much bigger. Consequently, there was a problem of shortening the battery life caused by its electric power consumption if the stimulation is always carried out for the left ventricle or for both the ventricles.

SUMMARY OF THE INVENTION

The present invention was made in consideration of the aforesaid problems and the purpose thereof is to propose a heart treatment equipment for treating a heart failure where, for example, the ventricle stimulation is optimized in order to inhibit the decrease of the cardiac output in response to the stimulation of the vagus nerve or heart rate increase.

Additionally, another purpose of the present invention is to propose a heart treatment equipment for treating a heart failure where the ventricle stimulation is controlled in accordance with the heart failure symptoms and the electric power consumption is reduced by lowering the operation rate of the stimulation for both the ventricles.

In order to achieve the aforesaid purpose, a heart treatment equipment according to the present invention comprises a right ventricle pulse generator for supplying a heart stimulation pulse to a first heart stimulating electrode provided in a right ventricle of the heart; a left ventricle pulse generator for supplying a heart stimulation pulse to a second heart stimulating electrode provided in a left ventricle of the heart; and a controller for selecting one of or both of the right ventricle pulse generator and the left ventricle pulse generator, wherein the controller selects both of the right ventricle pulse generator and the left ventricle pulse generator in response to the stimulation of a vagus nerve or the heart rate increase.

Further, one exemplified embodiment heart treatment equipment according to the present invention comprises right ventricle pulse generator for supplying a heart stimulation pulse to a first heart stimulating electrode provided in a right ventricle of the heart; left ventricle pulse generator for supplying a heart stimulation pulse to a second heart stimulating electrode provided in a left ventricle of the heart; a nerve stimulator for supplying a nerve stimulating pulse for stimulating a vagus nerve to a nerve stimulating electrode; and a controller for selecting one of or both of the right ventricle pulse generator and the left ventricle pulse generator, wherein the controller selects both of the right ventricle pulse generator and the left ventricle pulse generator in response to the nerve stimulator.

As a more preferred exemplified embodiment of a heart treatment equipment according to the present invention, the equipment is provided with an atrium event detector for detecting a spontaneous atrium contraction other than the above mentioned constitutions and added with an atrioventricular delay time measuring portion responsive to the atrium event detector for measuring time after a predetermined atrioventricular delay time so as to perform a ventricle stimulation.

In these heart treatment equipments of exemplified embodiments where a stimulation of a vagus nerve and stimulations of both ventricles are carried out in cooperation, it becomes possible to inhibit the lowering of the cardiac output based on the stimulation of the vagus and at the same time it becomes possible to stimulate the ventricle for each of heart failure patients at an optimum timing after the spontaneous contraction of the atrium.

Further, another exemplified embodiment of a heart treatment equipment according to the invention is characterized by comprising a right ventricle pulse generator for supplying a heart stimulation pulse to a first heart stimulating electrode provided in a right ventricle of the heart; a left ventricle pulse generator for supplying a heart stimulation pulse to a second heart stimulating electrode provided in a left ventricle of the heart; an atrium event detector for detecting a contraction of an atrium; an atrioventricular delay time measuring portion for measuring a delay time for triggering the ventricle stimulation after a predetermined atrioventricular delay time in response to the atrium event detector; a heart rate monitor for monitoring a heart rate; and a controller for selecting one of or both of the right ventricle pulse generator and the left ventricle pulse generator in response to the heart rate monitor.

As another modified exemplified embodiment of a heart treatment equipment according to the present invention, aforesaid heart rate monitor is not provided and the controller for selecting one of or both of the right ventricle pulse generator and the left ventricle pulse generator is made to select both of the right ventricle pulse generator and the left ventricle pulse generator when the interval of the triggers between the most recent ventricle stimulation and the ventricle stimulation is larger than a predetermined threshold value.

According to the heart treatment equipment of the present invention, either one of the ventricle stimulation modes of both ventricle stimulation and single ventricle stimulation is selected in accordance with the heart rate, so that the operation rate of the stimulation for both the ventricles is lowered and it is possible to reduce the electric power consumption.

DESCRIPTION OF THE PREFERRED EMBODIMENTS

Figure 1:
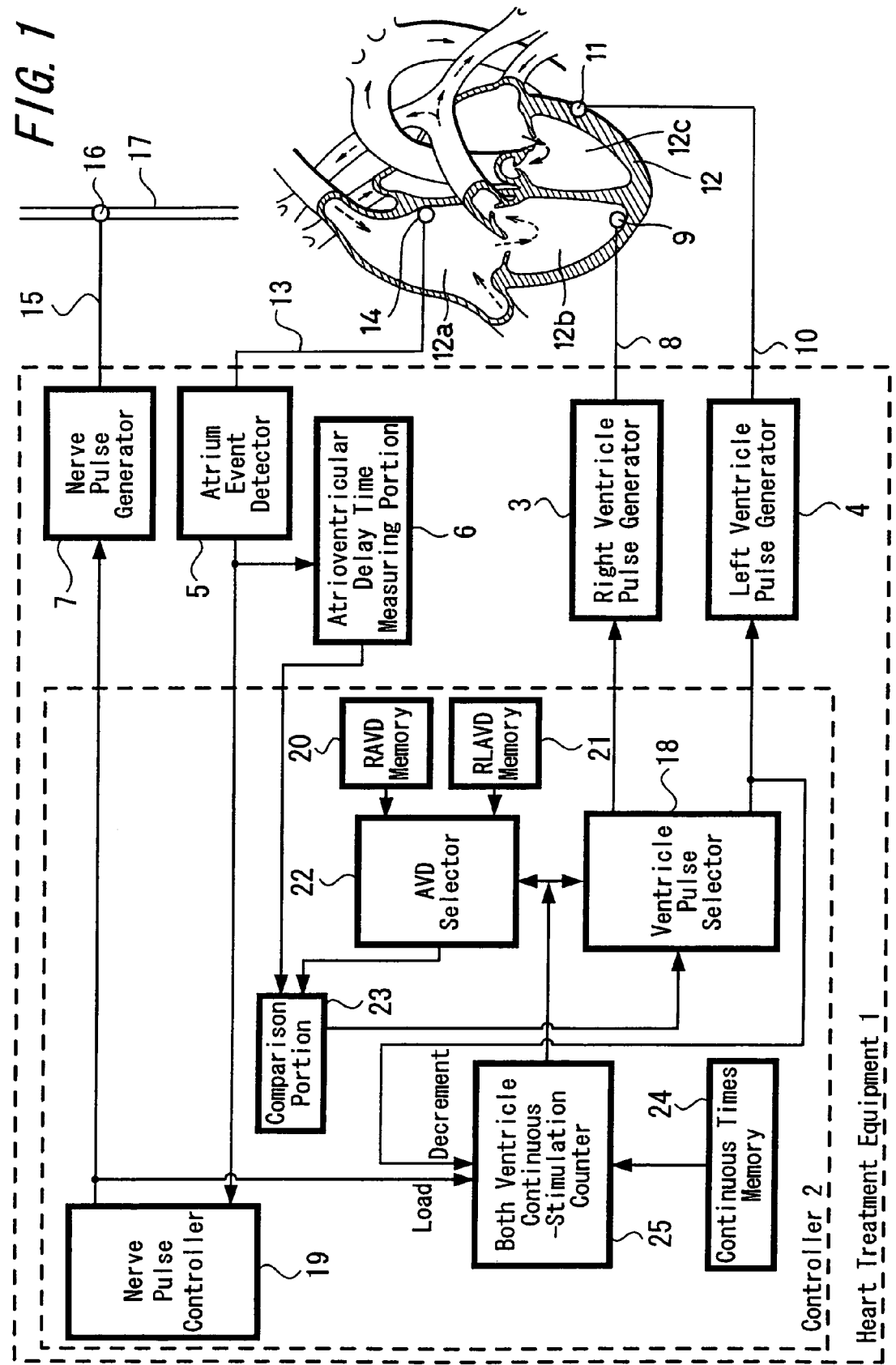
FIG. 1 is a diagram showing a constitutional example of a first exemplified embodiment of a heart treatment equipment according to the present invention.

A first exemplified embodiment of a heart treatment equipment according to the present invention will be precisely described in connection with FIG. 1. It should be noted that the term "event" of a heart in this specification includes any contraction phenomenon which arose in the heart (atrium and/or ventricle) regardless of a cause by stimulation and of a spontaneous cause.

A heart treatment equipment 1 is constituted by a controller 2, a right ventricle pulse generator 3 which generates a right ventricle stimulation pulse for stimulating the right ventricle of the heart, a left ventricle pulse generator 4 which generates a left ventricle stimulation pulse for stimulating the left ventricle of the heart, an atrium event detector 5 for detecting an atrium contraction of the heart (atrium event), an atrioventricular delay time measuring portion 6 responsive to the atrium event for measuring a predetermined time until when a ventricle stimulation pulse which stimulates the right ventricle or both of the right ventricle and the left ventricle is generated, and a nerve pulse generator 7 which generates a nerve stimulation pulse for stimulating the vagus nerve 17.

Figure 2:
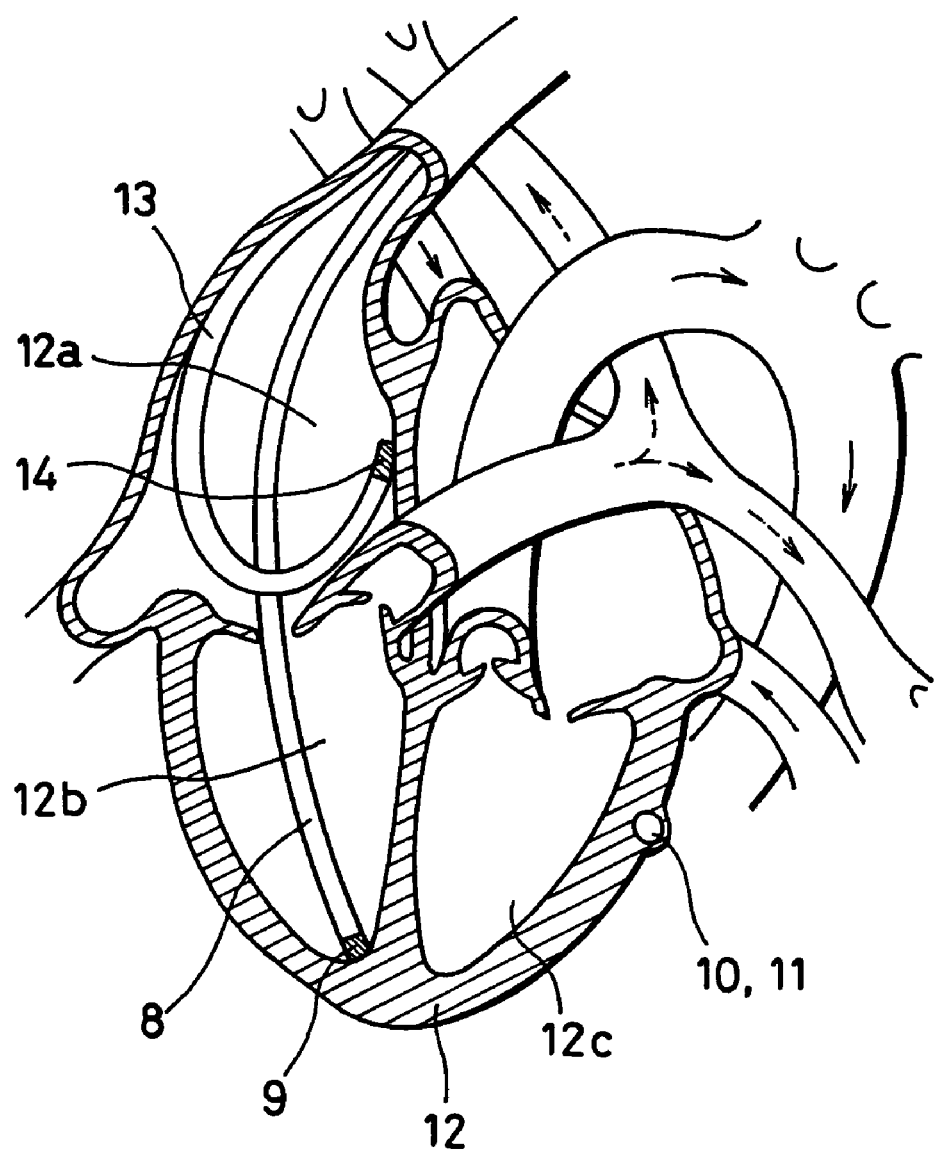
FIG. 2 is a layout diagram of a lead and an electrode with respect to a heart, which are used in a heart treatment equipment according to the present invention.

The right ventricle pulse generator 3 is connected to a right ventricle stimulating electrode 9 by means of a right ventricle lead 8, and the left ventricle pulse generator 4 is connected to a left ventricle stimulating electrode 11 by means of a left ventricle lead 10. Additionally, the atrium event detector 5 is connected to an atrium event detecting electrode 14 by means of an atrium lead 13. The right ventricle stimulating electrode 9, the left ventricle stimulating electrode 11 and atrium event detecting electrode 14 are arranged in the heart 12 as shown in FIG. 2.

Generally, as an electrode for a heart, there is an epicardium electrode embedded in a muscle of the heart and a catheter electrode which is an electrode inserted into the heart through a large vein. FIG. 2 shows an example of catheter electrodes where all of the right ventricle lead 8, the left ventricle lead 10 and the atrium lead 13 are introduced to the right atrium of the heart 12 firstly through a large vein.

The atrium lead 13 which is inserted to the right atrium through the large vein is inserted such as being hooked at its bended tip portion of J-shape in a right auricular appendage which protruded from the wall of the right atrium and has a pouched form and the atrium event detecting electrode 14 is arranged such as being contacted with the inner wall of the right auricular appendage. Additionally, the right ventricle lead 8 which is similarly inserted to the right atrium 15 through the large vein enters the right ventricle through an atrioventricular valve and the right ventricle stimulating electrode 9 which is provided at the tip portion of the right ventricle lead 8 is arranged such as being contacted with an appex of the right ventricle. Further, though not shown in FIG. 2, the left ventricle lead 10 passes the right atrium through the large vein and is inserted to a coronary sinus which has an opening at the right atrium or further is inserted to a coronary vein which has an opening at the coronary sinus, and the left ventricle stimulating electrode 11 is arranged such as being contacted with the left ventricle from the inside of the coronary vessel. The nerve pulse generator 7 is connected to a nerve stimulating electrode 16 by means of a nerve lead 15 and the nerve stimulating electrode 16 is fixed to a vagus nerve 17 by wrapping the latter.

The controller 2 of the heart treatment equipment 1 shown in FIG. 1 is constituted by a ventricle pulse selector 18 which is connected to both of the right ventricle pulse generator 3 and the left ventricle pulse generator 4; a nerve pulse controller 19 connected to the nerve pulse generator 7 and the atrium event detector 5; an RAVD memory 20 which memorize an atrioventricular delay time after the right atrium event occurs and until the right ventricle is stimulated; an RLAVD memory 21 for memorizing an atrioventricular delay time after the right atrium event occurs and until the right ventricle and the left ventricle are stimulated at the same time; an AVD selector 22 for selecting either one of the RAVD memory 20 and the RLAVD memory 21; a comparison portion 23 for generating an output when a counted value of the atrioventricular delay time measuring portion 6 reaches a set value of the RAVD memory 20 or the RLAVD memory 21 selected by the AVD selector 22; a continuous times memory 24 which memorizes beforehand how many times both the ventricles are stimulated; and both the ventricle continuous-stimulation counter 25 for decrementing the value set by the continuous times memory 24 whenever there is an output from the ventricle pulse selector 18 to the left ventricle pulse generator 4.

Then, the nerve pulse controller 19 is constituted so as to generate a control signal when the interval between the atrium events from the atrium event detector 5 or the average of the intervals between the atrium events becomes equal or lower than, for example, 750 ms which is a period corresponding to a situation where the heart rate is equal or more than 80 times per a minute. Additionally, in a case when both the ventricle continuous-stimulation counter 25 is loaded with a value which is set in the continuous times memory 24, the ventricle pulse selector 18 is constituted so as to select both of the right ventricle pulse generator 3 and the left ventricle pulse generator 4 and the AVD selector 22 is constituted so as to select the RLAVD memory 21. Further, in a case when the value of both the ventricle continuous-stimulation counter 25 becomes "0" it is constituted such that the ventricle pulse selector 18 selects only the right ventricle pulse generator 3 and the AVD selector 22 selects the RAVD memory 20.

Here, the time stored in the RAVD memory 20 is a preferable atrioventricular delay time after the right atrium event occurs until the right ventricle stimulation is performed for each heart disease patient: and the time stored in the RLAVD memory 21 is a preferable atrioventricular delay time after the right atrium event occurs until the stimulations of the right ventricle and the left ventricle are performed at the same time.

The operation of a first exemplified embodiment of a heart treatment equipment according to the present invention will be described hereinafter.

In FIG. 1, first the activity of the atrium which is detected by the atrium event detecting electrode 14 is transmitted to the atrium event detector 5 through the atrium lead 13. The atrium event detector 5 detects an atrium event from the transmitted activity of the atrium and transmits the detected atrium event signal to the nerve pulse controller 19.

When the detected atrium event signal is transmitted to the nerve pulse controller 19 from the atrium event detector 5, the nerve pulse controller 19 observes whether or not the event interval of every one cycle of the atrium or the average of the event intervals of several cycles becomes equal or less than, for example, 750 ms which is a period corresponding to a situation where the heart rate is equal or more than 80 times per a minute, and when it becomes equal or less than 750 ms, the nerve stimulation is judged to be necessary and a control signal is transmitted to the nerve pulse generator 7.

Here, the nerve pulse controller 19 catches the increase of the sympathetic nerve tone by the increase of the heart rate and operates to stimulate the vagus nerve 17 such that the sympathetic nerve tone is suppressed competitively and at the same time the oxygen consumption of the heart is decreased by decreasing the heart rate, so that the danger of an occurrence of a ventricular tachycardia and/or a ventricular fibrillation is reduced.

The control parameter of the vagus nerve stimulation is not limited to a case of the atrium event information and it can be a case of the ventricle event information, can be living body information such as cardiac information and hemodynamics information which represent the tone of the autonomic nerve, can be physical information such as an exercise intensity and an exercise duration, or can be a combination of these of information.

The nerve pulse generator 7 generates a nerve stimulating pulse by receiving a control signal from the nerve pulse controller 19 and stimulates the vagus nerve 17 by means of the nerve electrode lead 15 and the nerve stimulating electrode 16. Here, the nerve stimulating electrode 16 is arranged usually such as wrapping the vagus nerve 17. The region where the nerve stimulating electrode 16 is wrapped is preferably selected to be in a cervical region or at a right center position of the external carotid artery. Further, it is also possible to arrange the nerve stimulating electrode 16 so as to stimulate the vagus nerve 17 adjacent to a blood vessel wall by detaining a catheter electrode in the blood vessel. It is preferable to select the arrangement region in a subclavian vein.

Further, the atrium event detector 5 transmits the detected atrium event signal also to the atrioventricular delay time measuring portion 6. The atrioventricular delay time measuring portion 6 starts the measuring time by a trigger signal transmitted from the atrium event detector 5 and transmits its time information to the comparison portion 23 in the controller 2.

On the other hand, in the RAVD memory 20, it is stored with a preferable atrioventricular delay time of an appropriate value for each heart disease patient, for example, from 150 ms to 250 ms after the right atrium event occurs until the right ventricle stimulation. Additionally, in the RLAVD memory 21, it is stored with a value of an atrioventricular delay time after the right atrium event occurs until the right ventricle and the left ventricle are stimulated at the same time.

The AVD selector 22 selects one of the times stored in the RAVD memory 20 and the RLAVD memory 21 and supplies it to the comparison portion 23. Then, in the comparison portion 23, the measured time information from the atrioventricular delay time measuring portion 6, that is, an elapsed time after the atrium event occurs is compared with a preferred atrioventricular delay time stored in the RAVD memory 20 or the RLAVD memory 21 selected by the AVD selector 22.

Normally, the AVD selector 22 selects the RAVD memory 20 and in this case, the ventricle pulse selector 18 is connected only to the right ventricle pulse generator 3. Then, when the measured time information from the atrioventricular delay time measuring portion 6, that is, when the elapsed time after the atrium event occurs reaches the atrioventricular delay time stored in the RAVD memory 20 which is selected by the AVD selector 22, an output is obtained from the comparison portion 23, and the ventricle pulse selector 18 activates the right ventricle pulse generator 3 which was selected such that a right ventricle stimulating pulse is generated so as to stimulate the right ventricle of the heart 12 through the right ventricle lead 8 and the right ventricle stimulating electrode 9.

When the heart rate detected in the nerve pulse controller 19 becomes equal or more than 80 times per a minute, that is, when the cardiac interval duration becomes equal or less than 750 ms and subsequently when a control signal is supplied from the nerve pulse controller 19 to nerve pulse generator 7 such that the vagus nerve 17 is stimulated, a desirable ventricle stimulation number N which is stored in a continuous times memory 24 is loaded to the counter of both ventricle continuous-stimulation 25 correspondingly. In this time, the AVD selector 22 is switched to the RLAVD memory 21 and at the same time the ventricle pulse selector 18 selects both of the right ventricle pulse generator 3 and the left ventricle pulse generator 4.

Then, when the AVD selector 22 selects the RLAVD memory 21, the elapsed time from the atrium event which was measured in the atrioventricular delay time measuring portion 6 is compared in the comparison portion 23 with the set time stored in the RLAVD memory 21. More specifically, it is judged by the comparison portion 23 whether or not the elapsed time from the atrium event occurrence reaches the preferable atrioventricular delay time after the right atrium event occurs until both of the right ventricle and the left ventricle are simultaneously stimulated.

It is preferable to set the atrioventricular delay time in case of simultaneously stimulating both of the ventricles as an atrioventricular delay time shorter than that of stimulating only the right ventricle. It is because there is a possibility of a regurgitation of the blood at the atrioventricular valve if cooperative contractions of the atrium and the ventricle can not be attained when both the ventricles are simultaneously stimulated such that the regurgitation of the blood also becomes a cause of lowering a cardiac output. This is caused by a phenomenon that the contraction time of the ventricle becomes delayed and extended, because the cardiac conduction velocity in specialized cardiac muscle fibers called as a cardiac conduction system for rapidly propagating the impulse of the heart throughout the whole cardiac muscle is made delayed by the nerve stimulation. More specifically, the ventricle and the atrium conduct a pumping operation cooperatively, so that a stroke volume (quantity of blood which a heart pumps out by a single heartbeat) may lower when the ventricle contraction is delayed and the cooperation is destroyed. Consequently, in order to correct this substantial delay of the ventricle contraction, it becomes necessary to stimulate more promptly when both the ventricles are stimulated than when only the right ventricle is stimulated. For this purpose it is necessary to make the atrioventricular delay time shorter compared with that when only the right ventricle is stimulated so as to recover the delay of the ventricle contraction thereby.

When the measured time of the atrioventricular delay time measuring portion 6 reaches the preferable atrioventricular delay time after the right atrium event occurs until both of the right ventricle and the left ventricle are simultaneously stimulated, which is stored in the RLAVD memory 21, an output is obtained from the comparison portion 23 and is supplied to the ventricle pulse selector 18. At this time, as the ventricle pulse selector 18 selects both of the right ventricle pulse generator 3 and the left ventricle pulse generator 4, the stimulating pulse is supplied to the right ventricle stimulating electrode 9 and the left ventricle stimulating electrode 11 simultaneously through the right ventricle lead 8 and the left ventricle lead 10 by means of the right ventricle pulse generator 3 and the left ventricle pulse generator 4 and the right ventricle and the left ventricle are stimulated at the same time.

Figure 3:
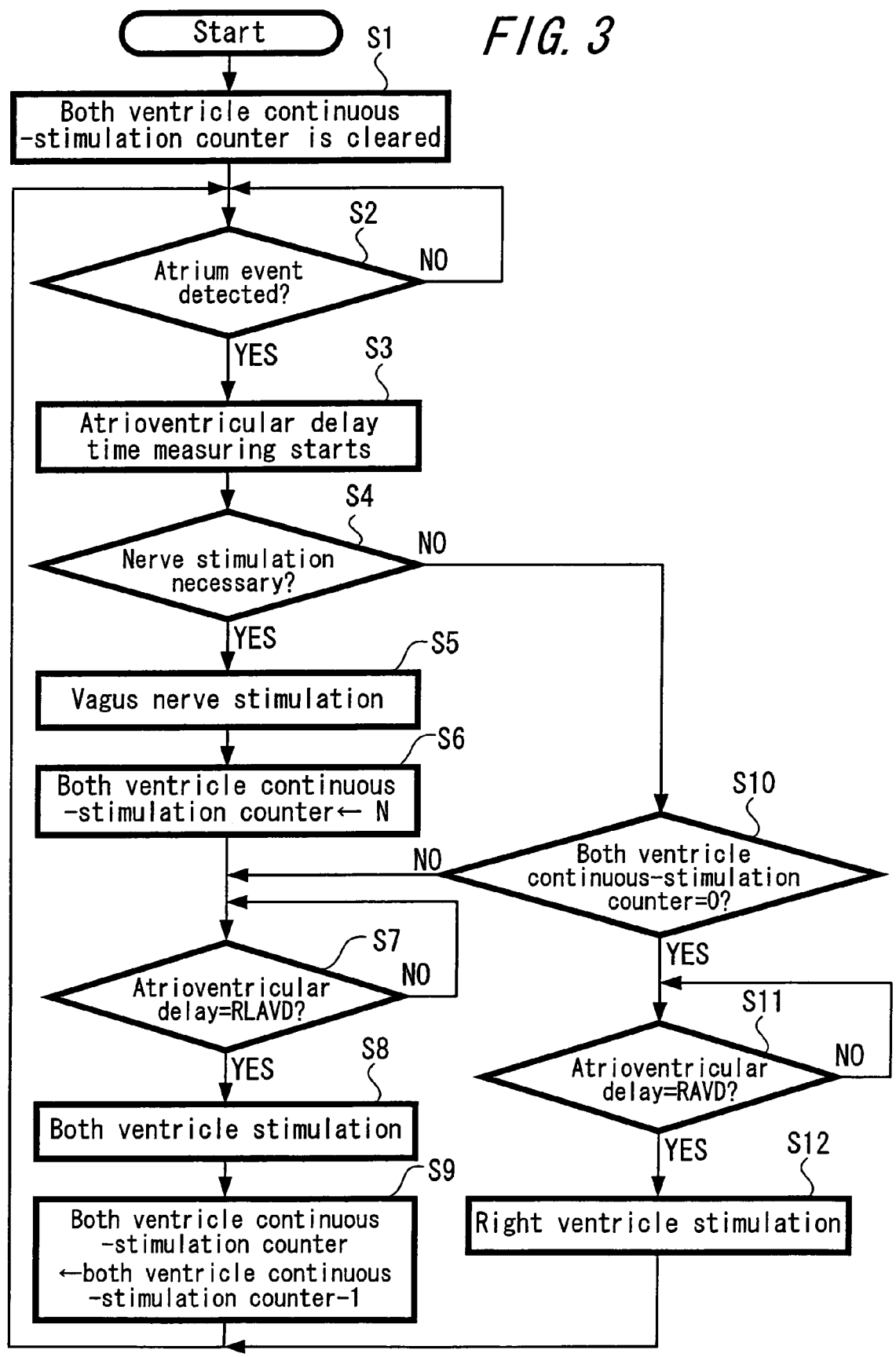
FIG. 3 is a flowchart showing an operation of the first exemplified embodiment of a heart treatment equipment according to the present invention shown in FIG. 1.

FIG. 3 is a flowchart showing the operational flow of the aforementioned first exemplified embodiment and the operation of this example will be explained in more detail using this flowchart. First, both the ventricle continuous-stimulation counter. 25 is made reset (step S1). When this both ventricle continuous-stimulation counter 25 is reset, the AVD selector 22 selects the RAVD memory 20 and the ventricle pulse selector 18 is connected only to the right ventricle pulse generator 3. Next, whether or not the atrium event is detected is judged by the atrium event detector 5 which observes the occurrence of the atrium event (step S2), and if the atrium event is not detected the cycle will be repeated. When the atrium event is detected, the atrioventricular delay time measuring portion 6 starts the time measuring (step S3) and at the same time the necessity of the nerve stimulation is judged in the nerve pulse controller 19 (step S4).

For example, when the average of the heart rate becomes equal or more than 80 and the detected number of the atrium events increases, it is judged that the nerve stimulation is necessary and the vagus nerve stimulation is performed (step S5), and at the same time a numerical value N which is stored in the continuous times memory 24 beforehand is loaded to both the ventricle continuous-stimulation counter 25 (step S6). At this time the AVD selector 22 selects the RLAVD memory 21 and the ventricle pulse selector 18 is connected to both the right ventricle pulse generator 3 and the left ventricle pulse generator 4. If it is judged that the nerve stimulation is not necessary in the judgment step S4, the flow advances to step S10.

When the numerical value N is loaded to both the ventricle continuous-stimulation counter 25 in step S6, it is judged next whether or not the time measured by the atrioventricular delay time measuring portion 6 comes to coincide with the set time stored in the RLAVD memory 21 (step S7). Then, when the time measured by the atrioventricular delay time measuring portion 6 reaches the time stored in the RLAVD memory 21, a ventricle stimulating pulse is transmitted to both of the right ventricle and the left ventricle simultaneously (step S8) When this stimulation of both the ventricles is performed simultaneously, the numerical value N loaded in both the ventricle continuous-stimulation counter 25 is subtracted by 1 and becomes (N−1) (step S9).

When it is judged in the judgment step S4 that the nerve stimulation is not necessary corresponding to such a situation when the heart rate is 80 or less and the like, it is judged whether or not the value of both the ventricle continuous-stimulation counter 25 is made "0" (step S10), and if the value of both the ventricle continuous-stimulation counter 25 is not "0", the flow returns to step S7.

When the stimulation of both the ventricles are repeated N times and the value of the counter of both ventricle continuous-stimulation 25 becomes "0", a signal is supplied from the counter of both ventricle stimulation 25 to the AVD selector 22 and the ventricle pulse selector 18, and the AVD selector 22 changes the output from the RLAVD memory 21 to the RAVD memory 20 and the ventricle pulse selector 18 changes the stimulation from the both ventricle, stimulation to only the right ventricle stimulation. At this time, it is judged in the judgment step S10 that the value of the counter of both ventricle continuous-stimulation 25 is "0" and the flow moves to a next step S11.

Then, it is judged in the judgment step S11 whether or not the measured time of the atrioventricular delay time measuring portion 6 reaches the set value of the atrioventricular delay time for the right ventricle stimulation which is stored in the RAVD memory 20, and when the measured time of the atrioventricular delay time measuring portion 6 reaches the aforesaid set value, a normal operation mode of a heart treatment equipment (conventional pacemaker operation mode) where the right ventricle stimulation pulse is generated from the right ventricle pulse generator 3 is regained (step S12).

Next, a second exemplified embodiment according to the present invention will be described with reference to FIG. 4 where the same reference-numerals are used for designating the same potions as those of the first exemplified embodiment according to the present invention shown in FIG. 2.

While the first exemplified embodiment of the present invention has a constitution where an output is obtained from both the ventricle continuous-stimulation counter 25 when N times of the both ventricle stimulation is performed continuously such that the AVD selector 22 and the ventricle pulse selector 18 are operated, the second exemplified embodiment of the present invention has a constitution where the AVD selector 22 and the ventricle pulse selector 18 are switched by means of a timer for measuring time instead of and corresponding to a counter for counting N times of the both ventricle stimulation.

Figure 4:
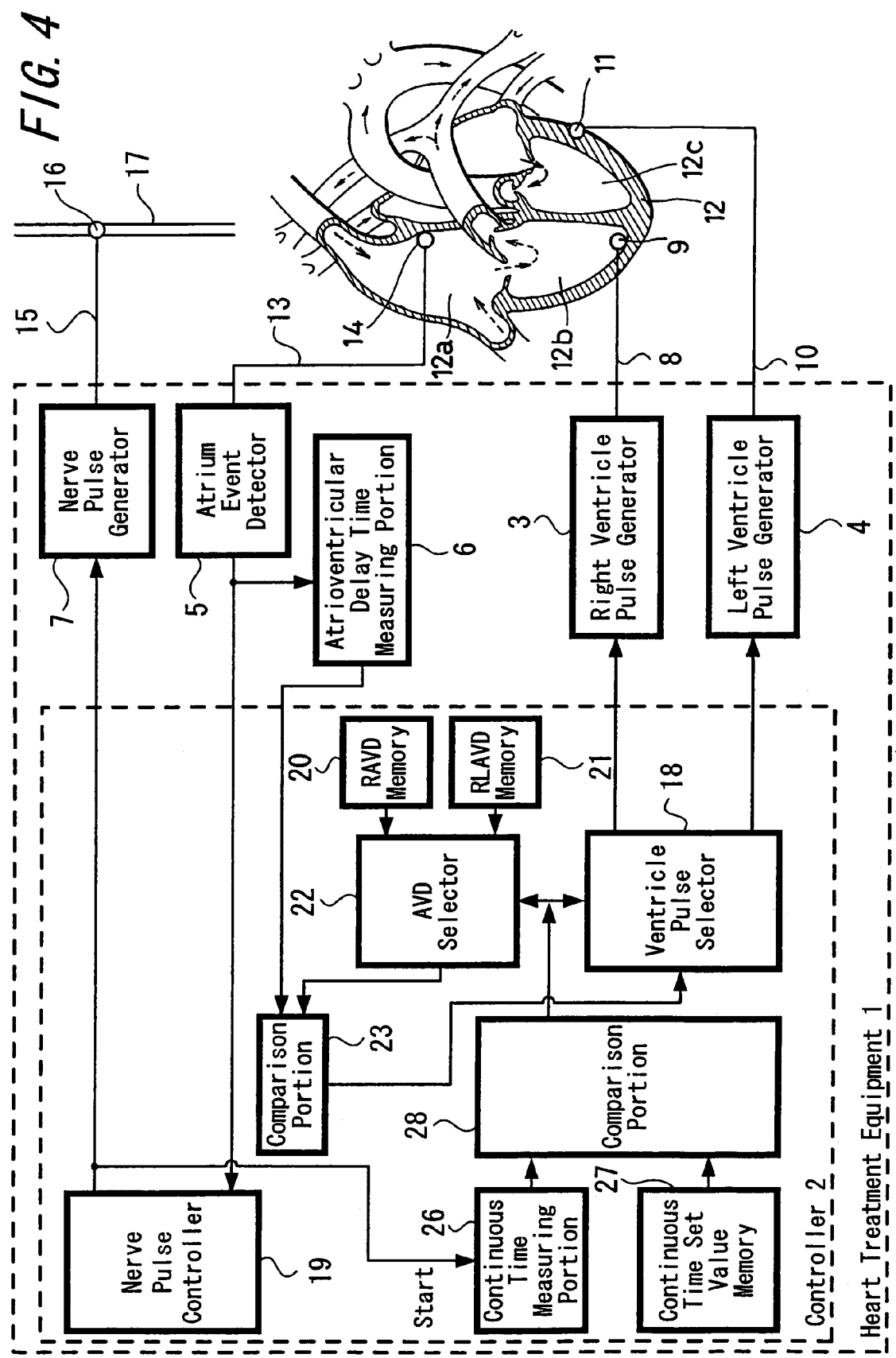
FIG. 4 is a diagram showing a constitutional example of a second exemplified embodiment of a heart treatment equipment according to the present invention.

More specifically, as shown in FIG. 4, the difference from the first exemplified embodiment of the present invention lies in that there is provided with a continuous time measuring portion 26 which starts counting in response to the generation of the nerve stimulating pulse; a continuous time set value memory 27 for presetting and storing a continuous time of stimulating the right ventricle and the left ventricle simultaneously; and a comparison portion 28 which judges whether or not the elapsed time from the nerve stimulation reaches the preset continuous time set value by comparing the outputs of the continuous time measuring portion 26 and the continuous time set value memory 27.

Similarly as the first exemplified embodiment of the present invention, first the activity of the atrium which is detected by the atrium event detecting electrode 14 is transmitted in the atrium event detector 5 through the atrium lead 13 and the atrium event detector 5 detects an atrium event from the transmitted activity of the atrium and transmits the detected atrium event signal to the nerve pulse controller 19. The nerve pulse controller 19 observes whether or not the interval of every one cycle of the detected atrium event signal or the average of the intervals of several cycles becomes equal or less than, for example, 750 ms which is a cardiac interval duration corresponding to a situation where the heart rate is equal or more than 80 times per a minute, and when it becomes equal or less than 750 ms, the nerve stimulation is judged to be necessary and a control signal is transmitted to the nerve pulse generator 7.

The continuous time measuring portion 26 starts counting of the elapsed time in response to this nerve stimulation and at the same time operates the AVD selector 22 and the ventricle pulse selector 18, so that the AVD selector 22 is switched such that it selects the RLAVD memory 21 instead of the RAVD memory 20 and the ventricle pulse selector 18 is switched such that it selects both of the right ventricle pulse generator 3 and the left ventricle pulse generator 4 instead of only the right ventricle pulse generator 3.

Additionally, when the atrium event is detected by the atrium event detector 5, the atrioventricular delay time measuring portion 6 also starts counting, and when the elapsed time reaches a preferable atrioventricular delay time which is, stored in the RLAVD memory 21 and corresponds to a time after the right atrium event occurs until the right ventricle and the left ventricle are simultaneously stimulated, an output can be obtained from the comparison portion 23 and is transmitted to both of the right ventricle pulse generator 3 and the left ventricle pulse generator 4 by means of the ventricle pulse selector 18, so that the stimulating pulse is supplied to the right ventricle stimulating electrode 9 and the left ventricle stimulating electrode 11 simultaneously through the right ventricle lead 8 and the left ventricle lead 10 such that the right ventricle and the left ventricle are simultaneously stimulated.

A preferable time for stimulating both of the right ventricle and the left ventricle of each heart disease patient is continuous set in the continuous time set value memory 27, the set time stored in aforesaid continuous time set value memory 27 and the elapsed time which is measured by the continuous time measuring portion 26 and corresponds to the time after the nerve stimulating pulse is generated are compared in the comparison portion 28, and when the elapsed time after the nerve stimulating pulse is generated reaches the set time stored in the continuous time set value memory 27, an output is obtained from the comparison portion 28 and is supplied to the AVD selector 22 and the ventricle pulse selector 18.

When the signal from this comparison portion 28 is received, the AVD selector 22 is switched such that the RAVD memory 20 is selected instead of the RLAVD memory 21 and the ventricle pulse selector 18 is switched such that only the right ventricle pulse generator 3 is selected instead of the both selection of the right ventricle pulse generator 3 and the left ventricle pulse generator 4. In this way, the heart treatment equipment 1 regains a normal operation mode of a heart treatment equipment (conventional pacemaker operation mode) where only the right ventricle is stimulated.

Figure 5:
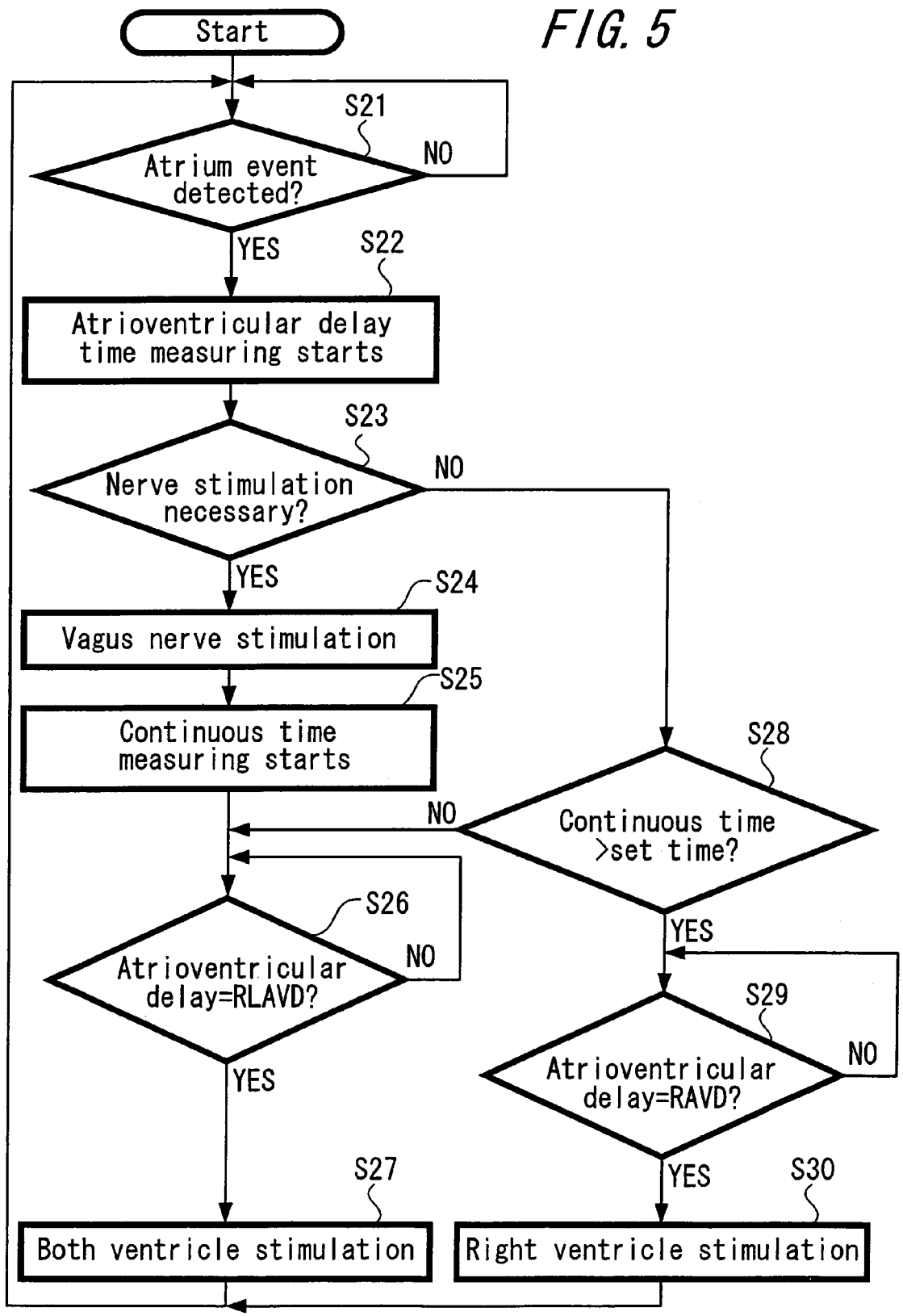
FIG. 5 is a flowchart showing an operation of the second exemplified embodiment of a heart treatment equipment according to the present invention shown in FIG. 4.

FIG. 5 is a flowchart showing the operational flow of the aforementioned second exemplified embodiment and the operation of the second exemplified embodiment will be explained in more detail using this flowchart. Under the initializing condition, the AVD selector 22 selects the RAVD memory 20 and the ventricle pulse selector 18 is connected only to the right ventricle pulse generator 3. First, whether or not the atrium event is detected is judged by the atrium event detector 5 which observes the occurrence of the atrium event (step S21), and if the atrium event is not detected the cycle will be repeated. When the atrium event is detected, the atrioventricular delay time measuring portion 6 starts the time measuring (step S22) and at the same time the necessity of the nerve stimulation is judged in the nerve pulse controller 19 (step S23).

For example, when the average of the heart rate becomes equal or more than 80 and the detected number of the atrium events increases, it is judged that the nerve stimulation is necessary and the vagus nerve stimulation is performed (step S24), and at the same time the continuous time measuring portion 26 starts counting (step S25). At this time the AVD selector 22 selects the RLAVD memory 21 and the ventricle pulse selector 18 is connected to both the right ventricle pulse generator 3 and the left ventricle pulse generator 4. If it is judged that the nerve stimulation is not necessary in the judgment step S23, the flow advances to step S28.

Next, it is judged whether or not the time measured by the atrioventricular delay time measuring portion 6 comes to coincide with the set time stored in the RLAVD memory 21 (step S26). Then, when the time measured by the atrioventricular delay time measuring portion 6 reaches the time stored in the RLAVD memory 21, a ventricle stimulating pulse is transmitted to both of the right ventricle and the left ventricle simultaneously (step S27).

When it is judged in the judgment step S23 that the nerve stimulation is not necessary corresponding to such a situation when the heart rate is 80 or less and the like, it is judged whether or not the measured time (continuous time) of the continuous time measuring portion 26 is longer than the set time of continuous time set value memory 27 (step S28) When the measured time (continuous time) of aforesaid continuous time measuring portion 26 is shorter than the set time of continuous time set value memory 27, the flow returns to step S26.

When the measured time (continuous time) of the continuous time measuring portion 26 exceeds the set time of the continuous time set value memory 27 in the judgment step S28, a signal is supplied from the comparison portion 28 to the AVD selector 22 and the ventricle pulse selector 18, and the AVD selector 22 changes the output from the RLAVD memory 21 to the RAVD memory 20 and the ventricle pulse selector 18 changes the stimulation from the both ventricle stimulation to only the right ventricle stimulation. The flow advances to step S29.

Then, it is judged in the judgment step S29 whether or not the measured time of the atrioventricular delay time measuring portion 6 reaches the set value of the atrioventricular delay time for the right ventricle stimulation which is stored in the RAVD memory 20, and when the measured time of the atrioventricular delay time measuring portion 6 reaches the aforesaid set value, a normal operation mode of a heart treatment equipment (conventional pacemaker operation mode) where the right ventricle stimulation pulse is generated from the right ventricle pulse generator 3 is regained (step S30)

Next, a third exemplified embodiment of a heart treatment equipment according to the present invention will be described with reference to FIG. 6 where the same reference numerals are used for designating the same potions as those of the first exemplified embodiment according to the present invention shown in FIG. 1 and the second exemplified embodiment according to the present invention shown in FIG. 4.

In both of the first exemplified embodiment according to the present invention shown in FIG. 1 and the second exemplified embodiment according to the present invention shown in FIG. 4, the right ventricle and the left ventricle are stimulated simultaneously when a nerve stimulation performs, but in the third exemplified embodiment according to the present invention, the stimulations of the right and left ventricle are to be performed with a time difference. In this example, the right ventricle is made stimulated first and the left ventricle is made stimulated later with a little time difference, but it should be noted that the left ventricle can be made stimulated first and the right ventricle can be made stimulated later conversely.

Figure 6:
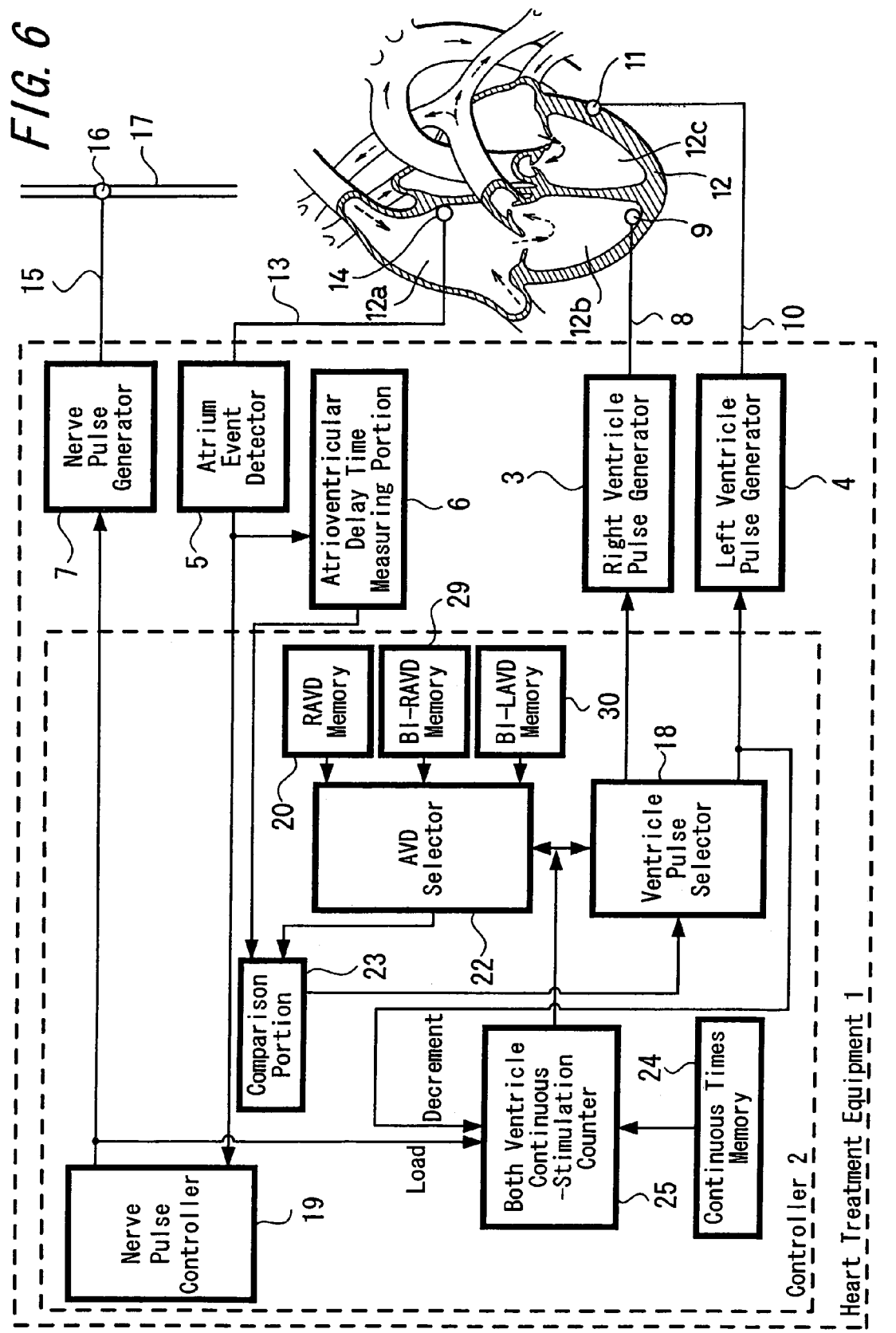
FIG. 6 is a diagram showing a constitutional example of a third exemplified embodiment of a heart treatment equipment according to the present invention.

In the third exemplified embodiment of the present invention shown in FIG. 6, a BI-RAVD memory 29 and a BI-LAVD memory 30 are provided instead of the RLAVD memory 21 used in the first or second exemplified embodiment according to the present invention. The BI-RAVD (atrium-right ventricle delay of biventricular pacing) memory 29 is provided for storing a preferable atrioventricular delay time after the detection of the right atrium event until the right ventricle stimulation for stimulating both of the ventricles and the BI-LAVD (atrium-left ventricle delay of biventricular pacing) memory 30 is provided for storing a preferable atrioventricular delay time after the detection of the right atrium event until the left ventricle stimulation for stimulating both of the ventricles.

The setting method of this atrioventricular delay time will be explained. In consideration of causes with respect to the decrease of acardiac output in case of a heart failure, there might be a lot of causes such as (1) a paradoxical movement of the ventricle based on a timing delay of the impulse conduction between the right and left ventricles, (2) a paradoxical movement of the ventricle based on organic change (hyperplasia and necrosis of the cardiac muscle, etc.) of the ventricular muscle, and the combination motion of 2 and 1.

First, for a patient having a cause of the decrease of a cardiac output based on the aforesaid (1), that is, a paradoxical movement of the ventricle based on a timing delay of the impulse conduction between the right and left ventricles, the timing delay is corrected by stimulating both of the ventricles simultaneously and the decrease of a cardiac output can be suppressed by a cooperative contraction of the right and left ventricles.

However, for a patient having a cause of the decrease of a cardiac output based on the aforesaid (2), that is, paradoxical movement of the ventricle based on organic change (hyperplasia and necrosis of the cardiac muscle, etc.) of the ventricular muscle (including a patient relating to a combination of (1) and (2)), the decrease of a cardiac output cannot always be suppressed even by stimulating both of the ventricles simultaneously, because the ventricular muscle which had an organic change cannot move cooperatively with the other normal ventricular muscle. In this case, it is necessary for the ventricular muscle which had an organic change that the participation thereof in the decrease of a cardiac output will be made reduced and it is further necessary to adjust the timing at which the stimulation pulse for the right ventricle and the left ventricle is sent so as to optimize the ventriclar contraction.

Realistically speaking, in order to perform such an adjustment, the vagus nerve stimulation is performed when the heart treatment equipment is implanted in the patient or when a periodic follow-up is done and the movement of the ventricle, an existence of the regurgitation of the blood at the atrioventricular valve and the like are observed by using such as an ultrasonic diagnostic equipment, and then it is necessary to set or adjust the stimulation timings of both the ventricles so as to make the lowering of the cardiac output decrease in response to the vagus stimulation be a minimum. In this way, the setting of the atrioventricular delay time must be precisely done in accordance with the condition of each heart failure patient.

The AVD selector 22 normally selects the RAVD memory 20, but when an atrium event is detected and as a result the vagus nerve 17 is stimulated, the AVD selector 22 changes from a mode where the RAVD memory 20 is selected to a mode where both of the BI-RAVD memory 29 and the BI-LAVD memory 30 are selected. At the same time, similarly as the first exemplified embodiment of the present invention shown in FIG. 1, a numerical value (e.g. N-times) which is stored in the continuous times memory 24 beforehand is set in both the ventricle continuous-stimulation counter 25 in response to the vagus nerve stimulation.

Here, it will be described hereinafter on the assumption that the atrioventricular delay time stored in the BI-RAVD memory 29 is shorter than the atrioventricular delay time stored in the BI-LAVD memory 30.

First, the measured time of the atrioventricular delay time measuring portion 6 reaches the time stored in the BI-RAVD memory 29, so that at this time an output of the comparison portion 23 is supplied to the right ventricle pulse generator 3 which is selected by the ventricle pulse selector 18. Then, the right ventricle pulse generator 3 supplies a stimulating pulse to the right ventricle stimulating electrode 9 through the right ventricle lead 8 and stimulates the right ventricle.

Subsequently, when the measured time of the atrioventricular delay time measuring portion 6 reaches the time stored in the BI-LAVD memory 30, an output from the comparison portion 23 is supplied to the left ventricle pulse generator 4 which is selected by the ventricle pulse selector 18 and a stimulating pulse is supplied to the left ventricle stimulating electrode 11 though the left ventricle lead 10 such that the left ventricle is stimulated.

At this time, "1" is subtracted from the numerical value N loaded in both the ventricle continuous-stimulation counter 25 every time when an output to the left ventricle pulse generator 4 is obtained Then, when the value of both the ventricle continuous-stimulation counter 25 becomes "0", an output is obtained from both the ventricle continuous-stimulation counter 25 and the output is given to the AVD selector 22 and the ventricle pulse selector 18 and the AVD selector 22 selects the RAVD memory 20, so that the ventricle pulse selector 18 is switched to a condition where only the right ventricle pulse generator 3 is selected.

In this way, according to this example, the right ventricle and the left ventricle are stimulated with a time difference after a predetermined time from the time when an atrium event is detected, so that an effective heart treatment equipment can be proposed especially for a patient when the paradoxical movement of the ventricle based on an organic change of the ventriclar muscle (hyperplasia and necrosis of the cardiac muscle, etc.) causes the decrease of a cardiac output and who cannot have a harmonic mechanical contraction of both the ventricles even by the simultaneous both ventriclar stimulation.

Figure 7:
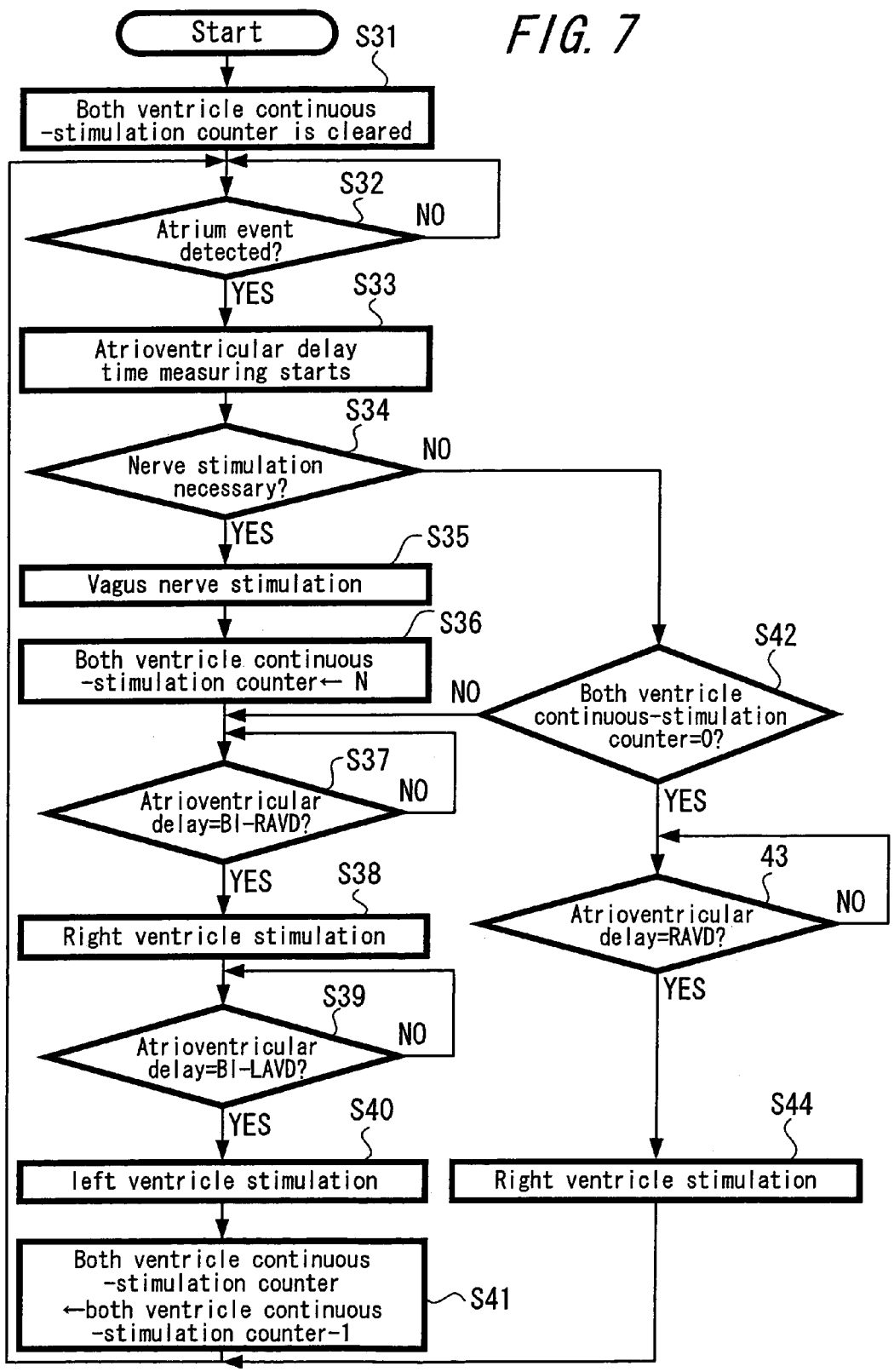
FIG. 7 is a flowchart showing an operation of the third exemplified embodiment of a heart treatment equipment according to the present invention shown in FIG. 6.

FIG. 7 is a flowchart showing the operational flow of the aforementioned third exemplified embodiment and the operation of the third exemplified embodiment according to the present invention will be explained in more detail by using this flowchart. First, both the ventricle continuous-stimulation counter 25 is made reset (step S31) When this both ventricle continuous-stimulation counter 25 is reset, the AVD selector 22 selects the RAVD memory 20 and the ventricle pulse selector 18 is connected only to the right ventricle pulse generator 3. Next, whether or not the atrium event is detected is judged by the atrium event detector 5 which observes the occurrence of the atrium event (step S32), and if the atrium event is not detected the cycle will be repeated. When the atrium event is detected, the atrioventricular delay time measuring portion 6 starts the time measuring (step S33) and at the same time the necessity of the nerve stimulation is judged in the nerve pulse controller 19 (step S34).

For example, when the average of the heart rate becomes equal or more than 80 and the detected number of the atrium events increases, it is judged that the nerve stimulation is necessary and the vagus nerve stimulation is performed (step, S35), and at the same time a numerical value N-which is stored in the continuous times memory 24 beforehand is loaded to both the ventricle continuous-stimulation counter 25 (step S36). If it is judged that the nerve stimulation is not necessary in the judgment step S34, the flow advances to step S42.

When the numerical value N is loaded to both the ventricle continuous-stimulation counter 25 in step S36, it is judged next whether or not the time measured by the atrioventricular delay time measuring portion 6 comes to coincide with the set time stored in the BI-RAVD memory 29 (step S37). If the elapsed time from the atrium event does not reach the set time stored in aforesaid BI-RAVD memory 29, the judgment step 37 is repeated until it reaches. Then, when the time measured by the atrioventricular delay time measuring portion 6 reaches the time stored in the BI-RAVD memory 29, a right ventricle stimulating pulse is emanated from the right ventricle pulse generator 3 (step S38). Subsequently, it is judged whether or not time measured by the atrioventricular delay time measuring portion 6 coincides with the set time stored in the BI-LAVD memory (step S39). If the elapsed time from the atrium event does not reach the set time stored in aforesaid BI-LAVD memory 30, the step 37 repeats until reached. Then, if the time measured by the atrioventricular delay time measuring portion 6 reaches the time stored in the BI-LAVD memory 30, a left ventricle stimulating pulse is generated from the left ventricle pulse generator 4 (step S40) Thereafter, when the stimulation of the left ventricle is performed, the numerical value N loaded in both the ventricle continuous-stimulation counter 25 is subtracted by 1 and becomes (N–1) (step S41).

When it is judged in the judgment step S34 that the nerve stimulation is not necessary corresponding to such a situation when the heart rate is 80 or less and the like, it is judged whether or not the value of both the ventricle continuous-stimulation counter 25 is made "0" (step S42), and if the value of both the ventricle continuous-stimulation counter 25 is not "0", the flow returns to step S37.

When the stimulation of both the ventricles are repeated N times and the value of the counter of both ventricle continuous-stimulation 25 becomes "0" in the judgment step S42, a signal is supplied from the counter of both ventricle continuous-stimulation 25 to the AVD selector 22 and the ventricle pulse selector 18, and the AVD selector 22 changes its output from a situation where both of the BI-RAVD memory 29 and the BI-LAVD 30 are selected to a situation where only the RAVD memory 20 is selected and the ventricle pulse selector 18 changes the situation from the both ventricle stimulation having a time difference to only the right ventricle stimulation. Then, it is judged in the judgment step S43 whether or not the time measured by the atrioventricular delay time measuring portion 6 coincides with the set time stored in the RAVD memory 20 and if the elapsed time from the atrium event does not reach the set time stored in aforesaid RAVD memory 20, the judgment step 43 is repeated until it reaches, and further if the time measured by the atrioventricular delay time measuring portion 6 reaches the time stored in the RAVD memory 20, a right ventricle stimulating pulse is generated from the right ventricle pulse generator 3 (step S44).

The aforesaid explanation relates to a case where both of the ventricles are stimulated after the atrium event is detected and where the right ventricle is first stimulated, but it is possible to stimulate the left ventricle first and to stimulate the right ventricle a little time later according to the condition of the heart disease patient.

Next, it will be described about a fourth exemplified embodiment according to the present, invention with reference to FIG. 8. The same reference numerals are used for designating the same potions as those in the first exemplified embodiment of the present invention shown in FIG. 1, the second exemplified embodiment of the present invention shown in FIG. 4 and the third exemplified embodiment of the present invention shown in FIG. 6.

In the first to the third exemplified embodiments according to the present invention, it is constituted that the ventricle pulse selector 18 and the AVD selector 22 are operated when a nerve stimulation performs such that a predetermined number of or a predetermined time of both the ventricle stimulation will be performed, but in the fourth exemplified embodiments according to the present invention, it is constituted that the ventricle pulse selector 18 and the AVD selector 22 are switched in accordance with the heart rate.

Figure 8:
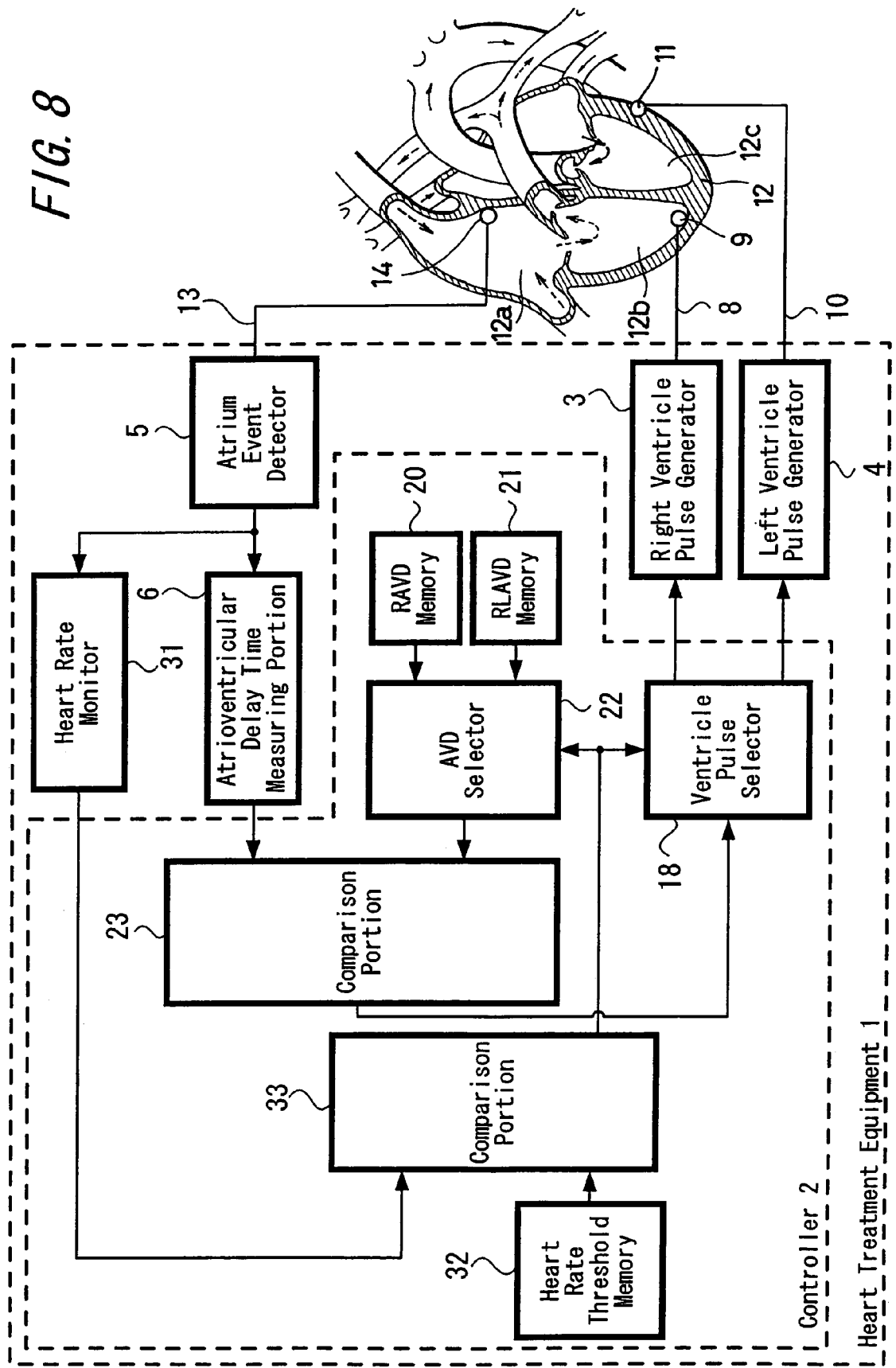
FIG. 8 is a diagram showing a constitutional example of a fourth exemplified embodiment of a heart treatment equipment according to the present invention.

More specifically, as shown in FIG. 8, the difference from the first to the third exemplified embodiments of the present invention lies in that there is provided with the: heart rate monitor 31 for measuring a heart rate from a detected atrium event, the heart rate threshold memory 32 for presetting:and storing a heart rate threshold value for simultaneous stimulating the right ventricle and the left ventricle, and the comparison portion 33 comparing outputs of the heart rate monitor 31 and the heart rate threshold memory 32 for judging whether or not the measured heart rate exceeds the preset threshold value, instead of the nerve pulse generator 7 and nerve pulse controller 19 used in the first to the third exemplified embodiments, the continuous times memory 24 and the counter of both ventricle continuous-stimulation 25 used in the first or third exemplified embodiment, the continuous time measuring portion 26 and the continuous time set value memory 27 used in the second exemplified embodiment.

First, the activity of the atrium which is detected by the atrium event detecting electrode 14 is transmitted in the atrium event detector 5 through the atrium lead 13 and the atrium event detector detects an atrium event from the transmitted activity of the atrium and transmits the detected atrium event signal to the heart rate monitor 31. The heart rate monitor 31 measures the atrium heart rate in accordance with the transmitted the atrium event signal and the measured heart rate is transmitted to the comparison portion 33. Here, the heart rate is defined as a heart rate per 1 minute.

The comparison portion 33 compares the heart rate transmitted from the heart rate monitor 31 and the threshold value stored in the heart rate threshold memory 32 and transmits information whether or not the measured heart rate goes over the threshold value to the ventricle pulse selector 18 and the AVD selector 22. It should be noted that the threshold value stored in the heart rate threshold memory 32 is different from a patient to a patient, but it is desirable to be 80 to 100 (times/a minute).

By receiving the signal from the comparison portion 33, the ventricle pulse selector 18 selects both the right ventricle pulse generator 3 and the left ventricle pulse generator 4 if the heart rate measured by the heart rate monitor 31 goes over the threshold value stored in the heart rate threshold memory 32 and if not, selects only the right ventricle pulse generator 3.

The AVD selector 22 receives the signal from the comparison portion 33 and when the heart rate measured by the heart rate monitor 31 exceeds the threshold value stored in the heart rate memory 32, it selects the RLAVD memory 21 in which a desirable atrioventricular delay time after a right atrium event occurs until a simultaneous stimulation for both the right ventricle and the left ventricle is performed is stored while if not, it selects the RAVD memory 20 in which a desirable atrioventricular delay time after a right atrium event occurs until only a right ventricle is stimulated is stored Further, the atrium event detector 5 also transmits the atrium event information detected through the atrium event detecting electrode 14 and the atrium lead 13 to the atrioventricular delay time measuring portion 6. The atrioventricular delay time measuring portion 6 starts the time measuring triggered by the transmitted event information from the atrium event detector 5 and transmits the measured time information to the comparator 23 of the controller 2.

The comparator 23 emanates an output to the ventricle pulse selector 18 when the measured time information from the atrioventricular delay time measuring portion 6, that is, the elapse time after the the atrium event occurs reaches the atrioventricular delay time stored in the RAVD memory 20 or the RLAVD memory 21 selected by the AVD selector 22. The ventricle pulse selector 18 instructs the selected pulse generator to generate a stimulation pulse triggered by the output of this comparator 23.

Figure 9:
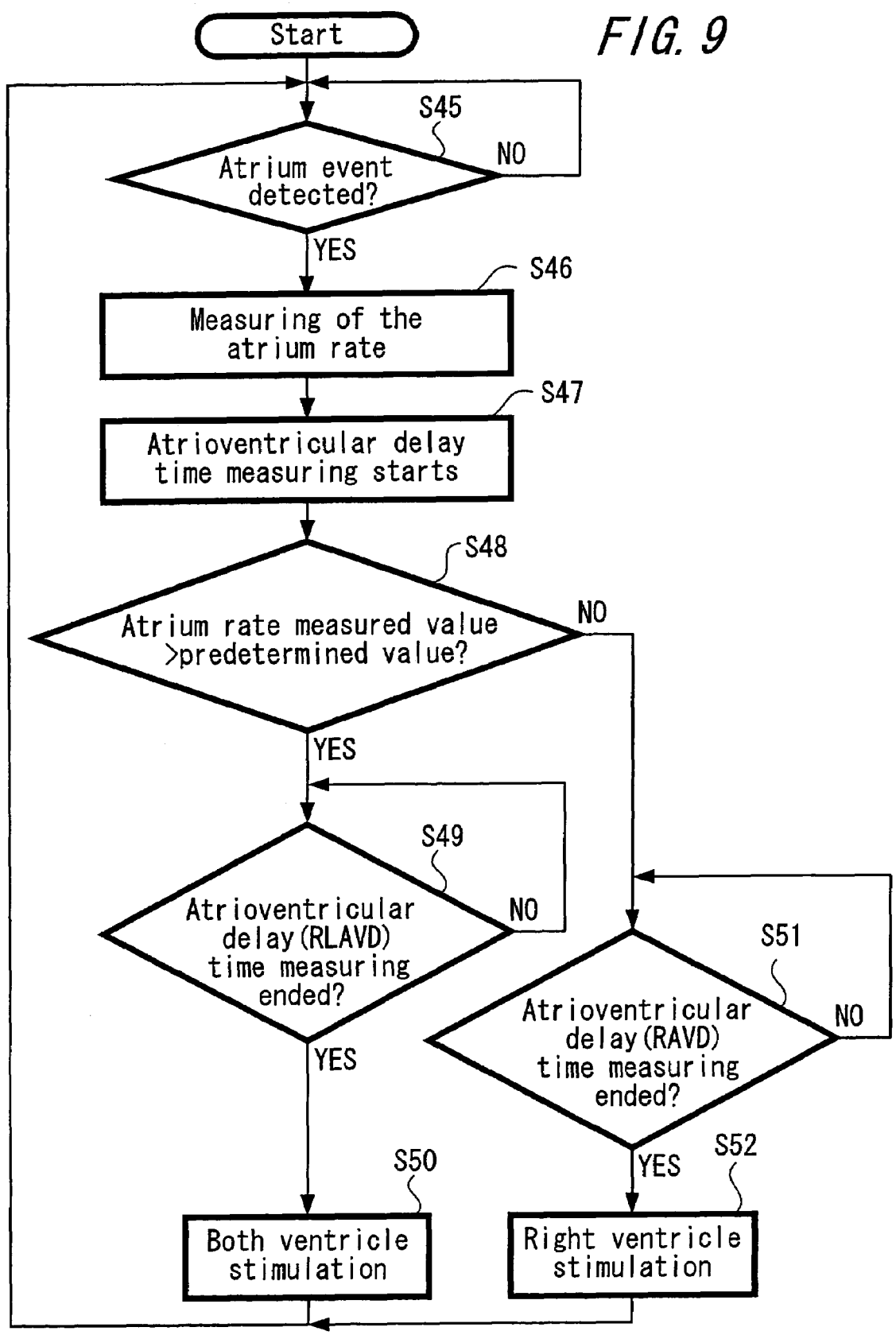
FIG. 9 is a flowchart showing an operation of the fourth exemplified embodiment of a heart treatment equipment according to the present invention shown in FIG. 8.

FIG. 9 is a flowchart showing the operation flow of aforementioned forth exemplified embodiment. Here, an equipment where an atrium rate is evaluated for the heart rate and when the atrium rate is below a predetermined value, the right ventricle stimulation is performed, and when the atrium rate goes over the predetermined value, the stimulation of both ventricles is performed will be explained.

First, when the occurrence of the atrium event is detected by the atrium event detector 5 (step S45), the measuring of the atrium rate is performed in the heart rate monitor 31 (step S46) and at the same time the atrioventricular delay time measuring portion 6 start measuring the atrioventricular delay time (step S47). In this case, at least two times of atrium events should be detected for measuring the atrium rate, so that the first measurement just after the equipment is operated will be ignored as a dummy measurement, etc. and formal measurement will be done after the second time. Here, the calculation equation for calculating the atrium rate R (times/minute) based on the-time t (seconds) between two consecutive atrium events is R=60/t. Additionally, the measured value of the atrium rate can be an instantaneous rate calculated from the information between the atrium events detected immediately before or can be an average rate calculated from the past atrium events of a predetermined number of cycles.

Subsequently, a threshold value (predetermined value) stored in the heart rate threshold memory 32 and the atrium rate measured in step 46 are compared-by the comparison portion 33 (step S48). When the atrium rate measured therein is higher than the threshold value, that is, when the heart rate is higher than the predetermined value, it is judged that the stimulation of both the ventricles should be performed and the AVD selector 22 selects the RLAVD memory 21 such that the comparison portion 23 observes until the output of the atrioventricular delay time measuring portion 6 reaches the value of the RLAVD memory 21 (step S49). Then, when the output of the atrioventricular delay time measuring portion 6 reaches the the set time stored in the RLAVD memory 21, the comparison portion 23 transmits a trigger signal to the ventricle pulse selector 18. The ventricle pulse selector 18 receives it and directs both of the right ventricle pulse generator 3 and the left ventricle pulse generator 4 to generate pulses such that both of the right and left ventricles are stimulated (step S50), and the flow returns to step 45. In this case, for the mode of the both ventricle stimulation, the right ventricle and the left ventricle can be simultaneously stimulated or one of the ventricle stimulation can go ahead first by setting a relative delay time between the right ventricle stimulation and the left ventricle stimulation.

Further, when the atrium rate measured in step 48 is below the threshold value, that is, when the heart rate is below a predetermined value, it is judged that the stimulation of only the right ventricle should be performed, so that the AVD selector 22 selects the value of the RAVD memory 20 and observes until the output of the atrioventricular delay time measuring portion 6 reaches the RAVD memory 20 by means of the comparison portion 23 (step S51). Then, when it reaches the set time stored in the RAVD memory 20, the comparison portion 23 transmits a trigger signal to the ventricle pulse selector 18. The ventricle pulse selector 18 receives it and directs the right ventricle pulse generator 3 to generate a pulse, so that the stimulation of only the right ventricle is performed (step S52). The flow returns to step 45 after the stimulation of the right ventricle is performed.

As mentioned above, according to the fourth exemplified embodiment of the present invention, the atrium rate is evaluated and when the atrium rate is below a predetermined value, the stimulation of only one ventricle (right ventricle) is selected, and when the atrium rate goes over the predetermined value, the both ventricle stimulation is selected. As a result, when an organic heart disease patient is under a physical exercise or when his heart rate increases because of a heart failure, it is possible to prevent the decrease of the cardiac output or the aggravation in his heart failure caused by the increase of the heart rate.

Figure 10:
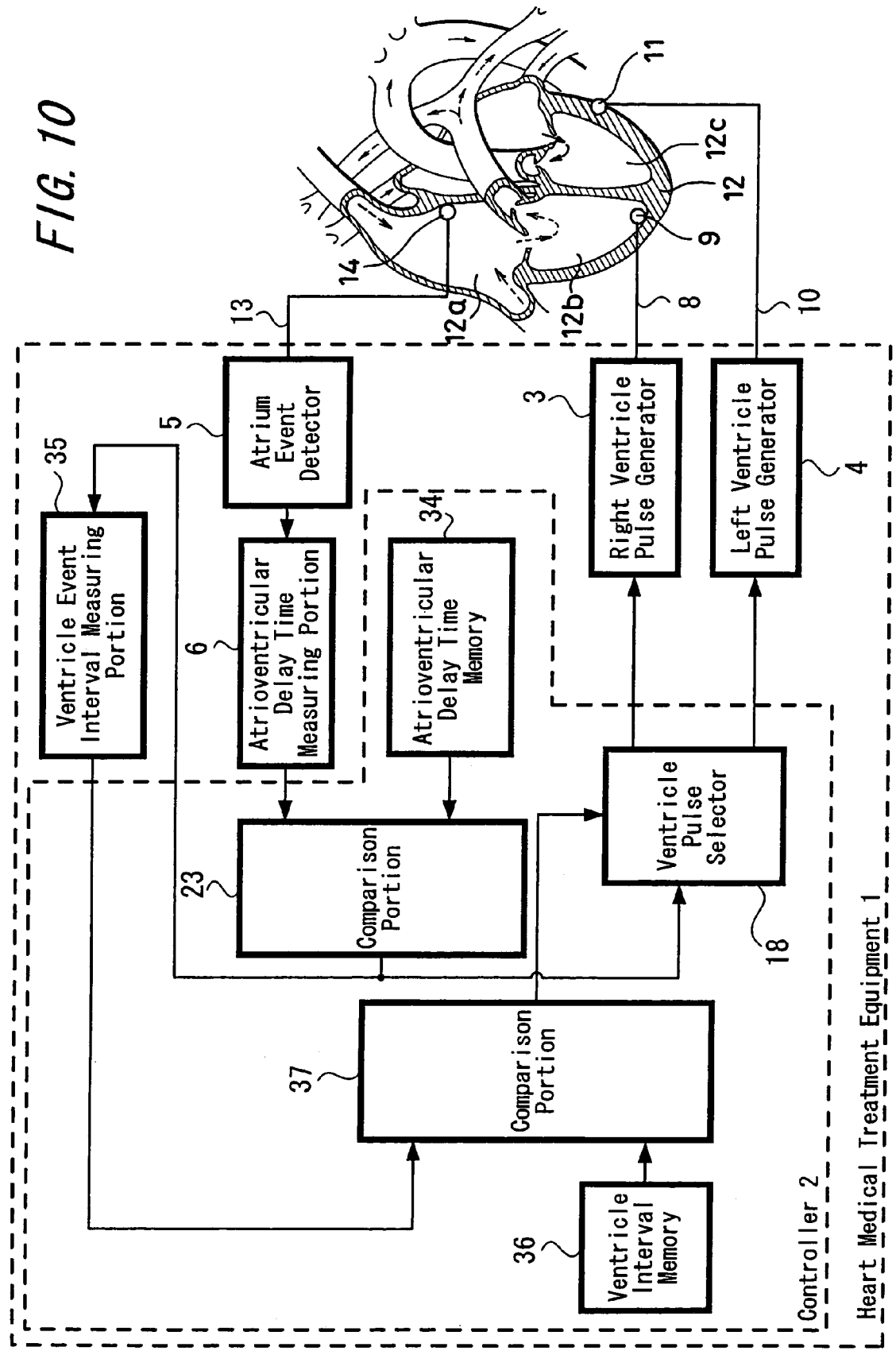
FIG. 10 is a diagram showing a constitutional example of a fifth exemplified embodiment of a heart treatment equipment according to the present invention.

Next, a constitution of a fifth exemplified embodiment of a heart treatment equipment according to the present invention will be described with reference to FIG. 10. Main differences from the fourth exemplified embodiment of the present invention shown in FIG. 8 lie in that there is provided with the ventricle event interval measuring portion 35 instead of the heart rate monitor 31. In FIG. 10, the same reference numerals are used for designating the same constitutional potions corresponding to those of the fourth exemplified embodiment shown in FIG. 4.

The heart treatment equipment 1 is constituted by a controller 2, the right ventricle pulse generator 3, the left ventricle pulse generator 4, the atrium event detector 5, an atrioventricular delay time measuring portion 6, and the ventricle event interval measuring portion 35.

The controller 2 is constituted by ventricle pulse selector 18 which is connected to both of the right ventricle pulse generator 3 and the left ventricle pulse generator 4; an atrioventricular delay time memory 34 (same as RAVD memory 20 of FIG. 8) which memorizes a preferable atrioventricular delay time after the right atrium event occurs and until the right ventricle is, stimulated; a comparison portion 23 for generating an output when the time measured by the atrioventricular delay time measuring portion 6 reaches the set value stored in the atrioventricular delay time memory 34; a ventricle interval memory 36 for storing a threshold value of the ventricle event interval; and a comparison portion 37 for comparing the output from the ventricle event interval measuring portion 35 and the threshold value stored in the ventricle interval memory 36.

The operation of a fifth exemplified embodiment of the present invention will be described hereinafter. The ventricle event interval measuring portion 35 measures the time of the ventricle event interval (interval of generating ventricle pulses) and the operation thereof is controlled by the controller 2.

The controller 2 includes a comparison portion 23 for receiving measured time information which the atrioventricular delay time measuring portion 6 starts measuring at the same time when the atrium event is detected, and the comparison portion 23 compares the set time stored in the atrioventricular delay time memory 34 and the measured time of the atrioventricular delay time measuring portion 6 and at the time when the measured time of the atrioventricular delay time measuring portion 6 coincides with the set time stored in the atrioventricular delay time memory 34, a trigger signal is transmitted to the ventricle event interval measuring portion 35.

The ventricle event interval measuring portion 35 measures the time on the basis of the trigger signal which is transmitted from the comparison portion 23. More specifically, it starts measuring the time at the same time when receiving the trigger signal and by receiving the next trigger signal, it outputs a time signal of a two consecutive signal interval to the comparison portion 37 and at the same time the time measuring is reset and restarted. The trigger signal directly becomes a trigger signal for generating the ventricle stimulating pulse as described hereinafter, so that the same result is obtained by measuring the time of the trigger signal interval as the case of measuring the ventricle stimulating pulse interval. Consequently, a ventricle event interval is to be transmitted to the comparison portion 37 every time when a trigger signal is emanated from the comparison portion 23. It should be noted that according to the fifth exemplified embodiment of the present invention, the measured value of "event interval" and not of "rate" is to be dealt with. The event interval can be the time between two consecutive events or can be an average interval obtained from the past ventricle events of predetermined cycles.

The comparison portion 37 compares a value of the ventricle event interval obtained from the ventricle event interval measuring portion 35 and the threshold value of the preset ventricle event interval stored in the ventricle interval memory 36 a signal whether or not the ventricle event interval is shorter than the threshold value is made to be sent to the ventricle pulse selector 18. The ventricle pulse selector 18 receives the signal and selects to stimulate both of the right and left ventricles simultaneously or to stimulate only one of the ventricles, and further controls the stimulating pulse generation of the right ventricle pulse generator 3 and/or the left ventricle pulse generator 4.

Figure 11:
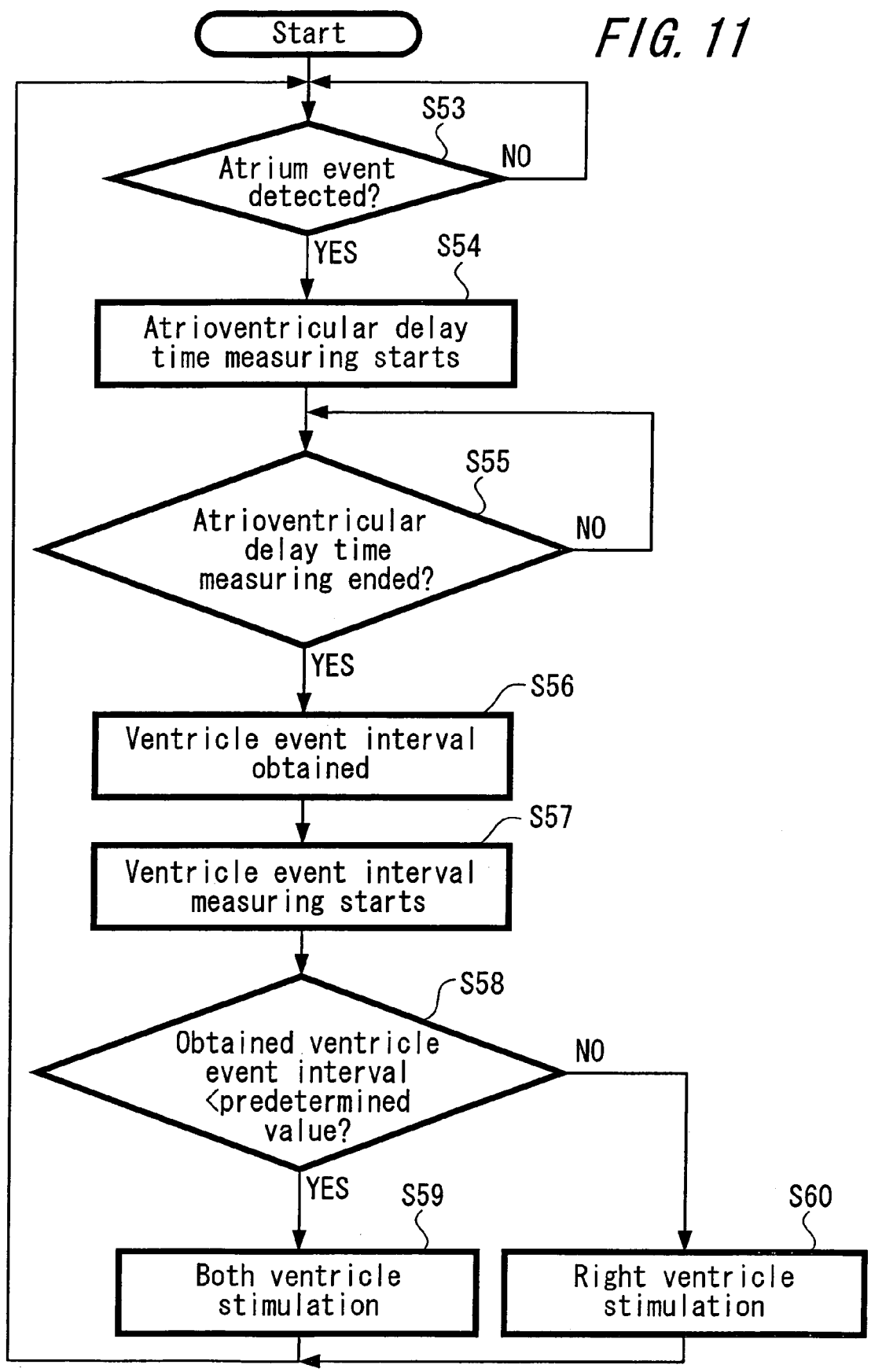
FIG. 11 is a flowchart showing an operation of the fifth exemplified embodiment of a heart treatment equipment according to the present invention shown in FIG. 10.

FIG. 11 is a flowchart showing the operation of the heart treatment equipment according to this exemplified embodiment. Here, the time interval of the last ventricle event and the pre-established ventricle stimulation is evaluated. An equipment will be explained where the simultaneous stimulation of both the ventricles is performed when the time interval is shorter than the predetermined value and the stimulation of only the right ventricle stimulation is performed when the time interval is longer than the predetermined value.

First, the atrium event detector 5 observes a occurrence of the atrium event and when the atrium event is detected (step S53), the atrioventricular delay time measuring portion 6 starts the time measuring of the atrioventricular delay time (step S54). Next, the comparison portion 23 waits until the measured time of the atrioventricular delay time measuring portion 6 reaches the set time stored in the atrioventricular delay time memory 34 (step S55), and a trigger signal is transmitted to the ventricle event interval measuring portion 35 The ventricle event interval measuring portion 35 obtains the time interval (ventricle event interval) between the last trigger signal and a trigger signal this time (step S56), and transmits it to the comparison portion 37. The ventricle event interval measuring portion 35 is reset at the same time and starts a new time measuring (step S57).

The comparison portion 37 compares the obtained value of ventricle event interval with a predetermined value (threshold value) stored in the ventricle interval memory 36 (step S58), and when the obtained value of the ventricle event interval is shorter than the predetermined value, the flow proceeds to step S59 and when the obtained value of the ventricle event interval is longer than the predetermined value, the flow proceeds to step S60.

In step S59, the ventricle event interval is shorter than the predetermined value, so that the stimulation of the right ventricle by the right ventricle pulse generator 3 through the right ventricle lead 8 and the right ventricle stimulating electrode 9 and the stimulation of the left ventricle by the left ventricle pulse generator 4 through the left ventricle lead 10 and the left ventricle stimulating electrode 11 are performed simultaneously, and the flow returns to step 53. In this case, for the mode of the both ventricle stimulation, the right ventricle and the left ventricle can be simultaneously stimulated or one of the ventricle stimulation can go ahead first by setting a relative delay time between the right ventricle stimulation and the left ventricle stimulation.

Additionally, instep S60, the ventricle event interval is longer than the predetermined value, so that the stimulation of only the right ventricle is performed by the right ventricle pulse generator 3 through the right ventricle lead 8 and the right ventricle stimulating electrode 9, and the flow returns to step S53.

As mentioned above, according to the fifth exemplified embodiment of the present invention, the time interval between the last ventricle event and the pre-established ventricle stimulation is evaluated and when the time interval is longer than a predetermined value, the stimulation of only one ventricle (right ventricle) is selected, and when the time interval is shorter than the predetermined value, the both ventricle stimulation is selected. As a result, when an organic heart disease patient is under a physical exercise or when his heart rate increases because of a heart failure, it is possible to prevent the decrease of the cardiac output or the aggravation in his heart failure caused by the increase of the heart rate.

As seen in the above, a heart treatment equipment according to the present invention was explained with reference to the exemplified embodiments shown in the drawings, but the present invention is not limited by these embodiments and can be applicable to any kinds of heart treatment equipments such as an implantable cardiac pacemaker and an implantable cardioverter defibrillator where a stimulating mechanism for both the ventricles is provided.

Further, in each of the aforementioned five exemplified embodiments, when one of the ventricles is stimulated, the stimulation of the right ventricle is selected, because the power consumption thereof can be relatively small, but it could be the stimulation of the left ventricle in response to the condition of the patient Furthermore, it is also possible to adopt a constitution where a detector connected to the electrodes of the right and left ventricles respectively is provided for observing a spontaneous-contraction of the right ventricle and the left ventricle such that a scheduled stimulation for the ventricle is inhibited when the spontaneous-contraction is detected.

As mentioned above, according to the present invention, it is designed as a ventricle stimulation method such that it can select a case where the stimulation of both the ventricles is performed or a case where only one of the ventricle is performed and the ventricle stimulation is performed in both of the right ventricle and the left ventricle in response to the vagus nerve stimulation or based on the heart rate, so that it can inhibit the decrease of the cardiac output caused by the vagus nerve stimulation or the heart rate increase. Further, the ventricle stimulation mode is selected from either one of the both ventricle stimulation and the single ventricle stimulation, so that the operation rate of the stimulation for both the ventricles is lowered and it is possible to reduce the electric power consumption.

Consequently, if the stimulation of both the ventricles is always performed, there arises a problem that the battery life and the device longevity are reduced because of the large power consumption thereof, but it is not necessary to perform the stimulation of both the ventricles while there are no symptoms of heart failure (for example, in a resting time) and the stimulation of both the ventricles should be performed when developing symptoms of heart failure (for example, during exercise). Accordingly, the power consumption can be lowered by inhibiting the stimulation of both the ventricles in response to the patient's situation and by lowering the operation rate of the stimulation for both the ventricles.

Having described preferred embodiments of the invention with reference to the accompanying drawings, it is to be understood that the invention is not limited to those precise embodiments and that various changes and modifications could be effected therein by one skilled in the art without departing from the spirit or scope of the invention as defined in the appended claims.

What is claimed is:

1. A heart treatment equipment comprising:
   a right ventricle pulse generator for supplying a heart stimulation pulse to a first heart stimulating electrode provided in a right ventricle of the heart;
   a left ventricle pulse generator for supplying a heart stimulation pulse to a second heart stimulating electrode provided in a left ventricle of the heart; and
   a controller for selecting one of or both of said right ventricle pulse generator and said left ventricle pulse generator, and
   a nerve stimulator for supplying a nerve stimulation pulse to a nerve stimulation electrode which stimulates a vagus nerve,
   wherein said controller selects both of said right ventricle pulse generator and said left ventricle pulse generator by detection of the stimulation to the vagus nerve, and the selection of both the ventricle pulse generators is performed for a predetermined number of times of the heart stimulations after said nerve stimulation.

2. A heart treatment equipment according to claim 1, wherein said nerve stimulator generates a nerve stimulation pulse when a heart rate exceeds a predetermined value.

3. A heart treatment equipment comprising:
   a right ventricle pulse generator for supplying a heart stimulation pulse to a first heart stimulating electrode provided in a right ventricle of the heart;
   a left ventricle pulse generator for supplying a heart stimulation pulse to a second heart stimulating electrode provided in a left ventricle of the heart;
   a nerve stimulator for supplying a nerve stimulating pulse to a nerve stimulating electrode which stimulates a vagus nerve; and
   a controller for selecting one of or both of said right ventricle pulse generator and said left ventricle pulse generator,
   wherein said controller selects both of said right ventricle pulse generator and said left ventricle pulse generator by detection of the stimulation to the vagus nerve, and the selection of both the ventricle pulse generators is performed for a predetermined time after nerve stimulation.

4. A heart treatment equipment according to claim 3, wherein the equipment further comprises an atrium event detector for detecting a spontaneous contraction of an atrium and atrioventricular delay time measuring portion responsive to said atrium event detector for measuring time after detecting the spontaneous contraction of the atrium.

5. A heart treatment equipment according to claim 4, wherein a ventricle stimulation is performed when one of said right ventricle pulse generator and said left ventricle pulse generator is selected and said atrioventricular delay time measuring portion is at a first atrioventricular delay time; and a ventricle stimulation is performed when both of said right ventricle pulse generator and said left ventricle pulse generator are selected and said atrioventricular delay time measuring portion is at a second atrioventricular delay time.

6. A heart treatment equipment according to claim 5, wherein said second atrioventricular delay time is shorter than said first atrioventricular delay time.

7. A heart treatment equipment according to claim 3, wherein the stimulations by said right ventricle pulse generator and said left ventricle pulse generator are performed at the same time for the ventricle stimulation where both of said right ventricle pulse generator and said left ventricle pulse generator are selected.

8. A heart treatment equipment according to claim 3, wherein said left ventricle pulse generator is operated for the ventricle stimulation subsequently to the operation of said right ventricle pulse generator after a predetermined time where both of said right ventricle pulse generator and said left ventricle pulse generator are selected.

9. A heart treatment equipment according to claim 3, wherein said right ventricle pulse generator is operated for the ventricle stimulation subsequently to the operation of said left ventricle pulse generator after a predetermined time where both of said right ventricle pulse generator and said left ventricle pulse generator are selected.

* * * * *